(12) United States Patent
Suter et al.

(10) Patent No.: US 8,372,622 B2
(45) Date of Patent: *Feb. 12, 2013

(54) MODIFIED VACCINIA VIRUS ANKARA FOR THE VACCINATION OF NEONATES

(75) Inventors: Mark Suter, Luzern (CH); Sabine Vollstedt, Bokhold-Hanredder (DE); Paul Chaplin, Munich (DE)

(73) Assignee: Bavarian Nordic A/S, Kvistgaard (DK)

( * ) Notice: Subject to any disclaimer, the term of this patent is extended or adjusted under 35 U.S.C. 154(b) by 32 days.

This patent is subject to a terminal disclaimer.

(21) Appl. No.: 13/006,824

(22) Filed: Jan. 14, 2011

(65) Prior Publication Data
US 2011/0159032 A1 Jun. 30, 2011

Related U.S. Application Data

(63) Continuation of application No. 12/607,585, filed on Oct. 28, 2009, now Pat. No. 7,892,533, which is a continuation of application No. 11/112,438, filed on Apr. 22, 2005, now Pat. No. 7,628,980, which is a continuation-in-part of application No. 10/418,854, filed on Apr. 18, 2003, now Pat. No. 7,097,842, which is a continuation-in-part of application No. PCT/EP01/13628, filed on Nov. 22, 2001.

(30) Foreign Application Priority Data

Nov. 23, 2000 (DK) ................................. 2000 01764
Apr. 19, 2002 (DK) ................................. 2002 00590

(51) Int. Cl.
*C12N 7/08* (2006.01)
*C12N 7/00* (2006.01)
*C12N 7/04* (2006.01)
*C12N 15/00* (2006.01)
*A61K 39/12* (2006.01)
*A61K 39/245* (2006.01)

(52) U.S. Cl. ... 435/237; 424/93.2; 424/93.6; 424/199.1; 424/232.1; 435/235.1; 435/236

(58) Field of Classification Search ........................ None
See application file for complete search history.

(56) References Cited

U.S. PATENT DOCUMENTS
3,914,408 A 10/1975 Mebus
(Continued)

FOREIGN PATENT DOCUMENTS
EP 1188834 A1 3/2002
GB 2370573 A1 7/2002
(Continued)

OTHER PUBLICATIONS

Mayr, A., Hochstein-Mintzel, V. & Stickl, H. Abstammung, Eigenschaften and Verwendung des attenuierten Vaccinia-Stammes MVA. Infection. 1975; 3, 6-14.*

(Continued)

*Primary Examiner* — Zachariah Lucas
*Assistant Examiner* — Stuart W Snyder
(74) *Attorney, Agent, or Firm* — Law Office of Salvatore Arrigo and Scott Lee, LLP

(57) ABSTRACT

The invention relates inter alia to a method for inducing a long-term protection in an animal against foreign antigens and tumor antigens comprising the step of administering to the animal at least one factor selected from type I interferons and Flt-3, and to a method for inducing a long-term increase of the number of dendritic cells in an animal comprising the step of administering to the animal a factor selected from type I interferon and Flt-3 and to a method of inducing or enhancing the maturation and/or for the activation of the immune system of an animal comprising the step of administering to the animal a factor selected from type I interferon and Flt-3.

20 Claims, 8 Drawing Sheets

Figure 1A:
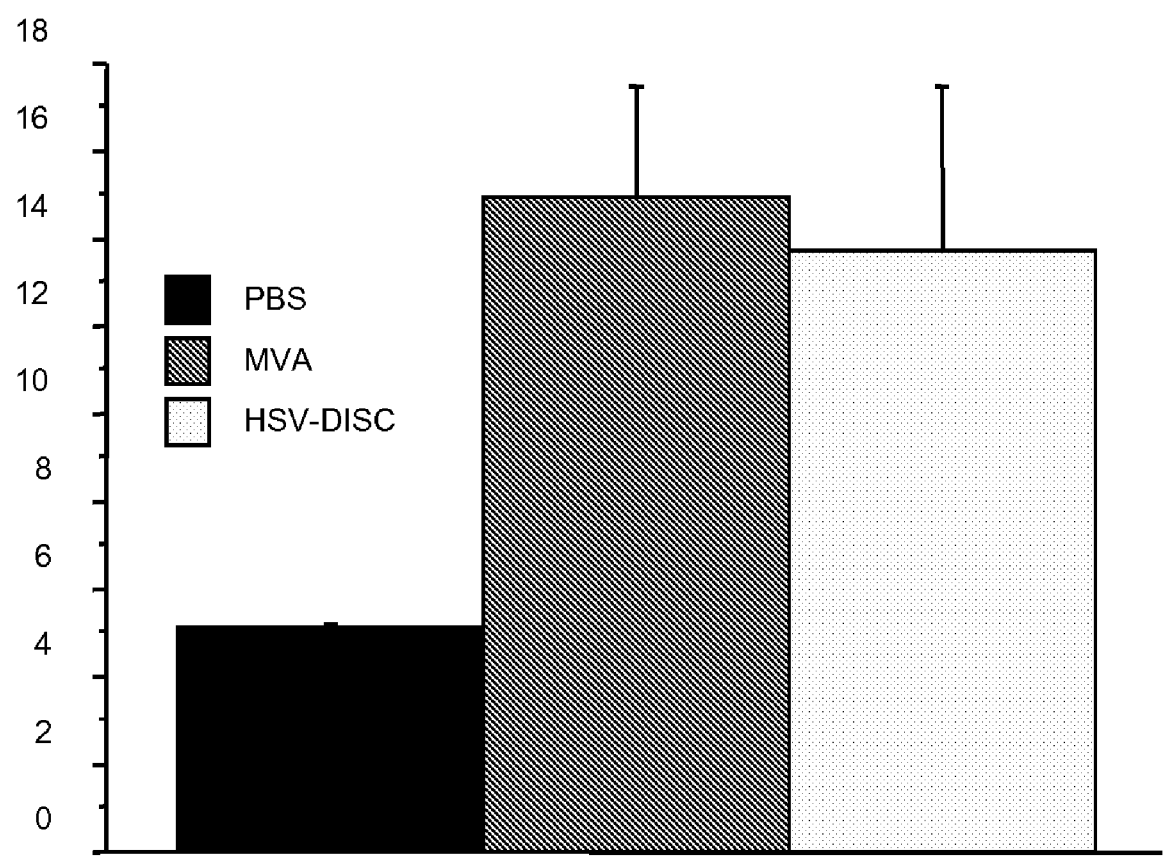

CD11c cells in 2 w old mice after MVA treatment

| Experiment BN9 | | blood | | spleen | |
|---|---|---|---|---|---|
| | n | % CD11c | % CD11c CD8 | % CD11c | % CD11c CD8 |
| naïve | 3 | 3.5 | 0.4 | 4.9 | 1.3 |
| 1 Vaccination at birth | 3 | 7.4 | 2.1 | 16.1 | 2.0 |
| 1 vaccination at d7 | 4 | 21.5 | 17.0 | 4.4 | 17.6 |
| 2 vaccination d 0 and 7 | 4 | 42.7 | 35.6 | 27.9 | 25.7 |

U.S. PATENT DOCUMENTS

| | | | |
|---|---|---|---|
| 4,191,745 | A | 3/1980 | Mayr et al. |
| 5,338,683 | A | 8/1994 | Paoletti |
| 5,403,582 | A | 4/1995 | Nazerian et al. |
| 5,405,772 | A | 4/1995 | Ponting |
| 5,753,489 | A | 5/1998 | Kistner et al. |
| 5,756,341 | A | 5/1998 | Kistner et al. |
| 5,770,212 | A | 6/1998 | Falkner et al. |
| 5,843,456 | A | 12/1998 | Paoletti et al. |
| 6,190,655 | B1 | 2/2001 | Lyman et al. |
| 6,204,250 | B1 | 3/2001 | Bot et al. |
| 6,605,465 | B1 | 8/2003 | Paoletti |
| 6,685,950 | B2 | 2/2004 | Weber et al. |
| 6,761,893 | B2 | 7/2004 | Chaplin et al. |
| 6,805,870 | B1 | 10/2004 | Mayr et al. |
| 6,913,752 | B2 | 7/2005 | Chaplin et al. |
| 7,097,842 | B2 * | 8/2006 | Suter et al. ............... 424/199.1 |
| 7,189,536 | B2 | 3/2007 | Chaplin et al. |
| 7,384,644 | B2 | 6/2008 | Chaplin et al. |
| 7,445,924 | B2 | 11/2008 | Chaplin et al. |
| 7,628,980 | B2 | 12/2009 | Suter et al. |
| 7,892,533 | B2 * | 2/2011 | Suter et al. ................. 424/93.6 |
| 7,923,017 | B2 | 4/2011 | Chaplin et al. |
| 7,939,086 | B2 | 5/2011 | Chaplin et al. |
| 8,163,293 | B2 * | 4/2012 | Chaplin ................... 424/199.1 |
| 2005/0214323 | A1 | 9/2005 | Chaplin et al. |
| 2005/0260156 | A1 | 11/2005 | Suter et al. |
| 2006/0127984 | A1 | 6/2006 | Ackermann et al. |
| 2006/0280758 | A1 | 12/2006 | Chaplin et al. |
| 2008/0089907 | A1 | 4/2008 | Chaplin et al. |
| 2009/0104224 | A1 | 4/2009 | Ackermann et al. |
| 2009/0169579 | A1 | 7/2009 | Chaplin et al. |
| 2010/0119545 | A1 | 5/2010 | Chaplin et al. |
| 2011/0135683 | A1 | 6/2011 | Chaplin et al. |
| 2011/0182932 | A1 | 7/2011 | Chaplin et al. |

FOREIGN PATENT DOCUMENTS

| | | | |
|---|---|---|---|
| WO | 90/12882 | A1 | 11/1990 |
| WO | 95/22978 | A1 | 8/1995 |
| WO | 97/02355 | A1 | 1/1997 |
| WO | 97/31119 | A1 | 8/1997 |
| WO | 98/13500 | A2 | 4/1998 |
| WO | 98/17283 | A1 | 4/1998 |
| WO | 98/56919 | A2 | 12/1998 |
| WO | 99/07869 | A1 | 2/1999 |
| WO | 00/29428 | A1 | 5/2000 |
| WO | 01/68820 | A1 | 9/2001 |
| WO | 01/89559 | A1 | 11/2001 |
| WO | 01/95919 | A2 | 12/2001 |
| WO | 02/24224 | A2 | 3/2002 |
| WO | 02/42480 | A2 | 5/2002 |
| WO | WO 2007/104581 | A1 | 9/2007 |
| WO | WO 2008/061939 | A1 | 5/2008 |

OTHER PUBLICATIONS

Blanchard et al., Modified vaccinia virus Ankara undergoes limited replication in human cells and lacks several immunomodulatory proteins: implications for use as a human vaccine, Journal of General Virology (1998), 79, 1159-1167.

Vossius & Partners, Opposition to EP Patent No. 1335987, D90, Response, Aug. 9, 2010.

Altenberger et al., Partial deletion of the human host range gene in the attenuated vaccinia virus MVA, Archives of Virology 15-27 (1989).

Stittelaar et al., Safety of modified vaccinia Ankara (MVA) in immune-supressed macaques, Vaccine 19:3700-3707 (2001).

Potter Clarkson, Grounds of Appeal, Opposition to EP 1335987, Jul. 25, 2011.

Janeway et al., T Cell-Mediated Immunity, Immunobiology 8:295-340 (2001).

Wyatt et al., Marker Rescue of the Host Range Restriction Defects of Modified Vaccinia Virus Ankara, Virology 251: 334-342 (1998).

EPO Opposition Division, Interlocutory Decision, D67, Opposition to EP Patent No. 1335987, Dec. 7, 2011.

B. Vilsmeier, Paraimmunity inducing effects of vaccinia strain MVA. (1999) Bed. Munch. Tierarztl. Wschr. 112:329-333.

A. Mayr. Paraspeziifsche Vaccinen aus Pockenviren (Paramunitatsinducer): eine neue Art von Impfstoll (1999) Azrtezeitschrift fur Naturheilverfahren 40, 8 pp. 550-557.

M. Franchini, et al., Protective T-Cell-Based Imminity Induced in Neonatal Mice by a Single Replicative Cycle of Herpes Simplex Virus. (2001) Journal of Virology 75:83-89.

K. Stittelaar. et al. Protective Immunity in Macaques Vaccinated with a Modified Vaccinia Virus Ankara-Based Measles Virus Vaccine in the Presence of Passively Acquired Antibodies. (2000) Journal of Virology 74:4236-4243.

A. Mayr Zbl. Vet. Med. B, TC marker of the attenuated vaccinia vaccide strain "MVA" in human cell cultures and protective immunization against orthopox diseases in animals. (1976) 23:417-430.

A. Bot. et al. Induction of immunological memory in baboons primed with DNA vaccine as neonates. (2001) Vaccine 19:1960-70.

C. McLean. et al. Induction of a protective immune response by mucosa{ vaccination with a DISC HSV-1 vaccine. (1996) Vaccine 14:987-92.

M. Monteil.et al. Effective priming of neonates born to immune dams against the immunogenic pseudorabies virus glycoprotein gD by replication-incompetent adenovirus-mediated gene transfer at birth. (1997) Journal of General Virology 78:3303-10.

C. Siegrist Vacciniation in the neonatal period and early infancy. Int. Rev Immunol. 19:195-219, 2000.

I. Belyakov. et al. Shared modes of protection against poxvirus infection by attenuated and conventional smallpox vaccine viruses. Proc. Natl. Acad. Sci. USA 100:9458-63, 2003.

Zhu et al., Evaluation of Recombinant Vaccinia Virus—Measles Vaccines in Rhesus Macaques with Preexisting Measles Antibody, Virology 276:202-213, 2000.

Kovarik et al., Induction of Adult-like Antibody, Th1, and CTL Responses to Measles Hemagglutinin by Early Life Murine Immunization with an Attenuated Vaccinia-Derived NYVAC (KIL) Viral Vector, Virology 285:12-20, 2001.

Dadaglio et al., Efficient In Vivo Priming of Specific Cytotoxic T Cell Responses by Neonatal Dendritic Cells, J. Immmunology 168:2219-2224, 2002.

Ridge et al., Neonatal Tolerance Revisited: Turning on Newborn T Cells with Dendritic Cells, Science 271:1723-1726, 1996.

Antoine et al. The Complete Genomic Sequence of the Modified Vaccinia Ankara Strain: Comparison with Other Orthopoxviruses. Virology 1998; 244:365-396.

Wyatt et al. Priming and boosting immuni7to tespiratory syncytial virus by recombinant replication-defective vaccinia virus MVA. Vaccine. 1999;18(5.-6):392-397.

Maraskovsky et al. Dramatic Increase in the Numbers of Functionally Mature Dendritic Cels in Flt2 Ligand-treated Mice: Multiple Dendritic Cell Subpopulations Identified. J Exp Med. 1996; 184:1953-1962.

Mayr et al. The Smallpox Vaccination Strain MVA: Marker, Genetic Structure, Experience Gained with the Parenteral Vaccine and Behavior in Organisms with a Debilitated Defence Mechansim. Zbl. Bakt. Hyg., I. Abt. Orig. B. 1978;167:375-390.

Musch et al. Phase II clinical trial of combined natural interferon-beta plus recombinat interferon-gamma treatment of chronic hpatitis B. Hepatogastroenterology. 1998; 45(24):2282-94.

Sayers et al. Antitumor Effects of alpha-interferon and gamma-Interferon on a Murine Renal Cancer (Renca) in Vitro and in Vivo. Cancer Research. 1990; 50: 5414-5420.

Marchant and Goldman. T cell-mediated immune responses in human newborns: ready to learn? Clinical and Experimental Immunology. Clinical and Experimental Immunology. 2005; 141: 10-18.

Goerner, et al., Expansion and Transduction of Nonenriched Human Cord Blood Cells Using HS-5 Conditioned Medium and FLT3-L. Journal of Hematotherapy & Stem Cell Research 9:759-765 (2000).

Murphy, et al. Prevention of Pertussis, Tetanus, and Diphtheria Among Pregnant and Postpartum Women and Their Infants. MMWR. 2008; 57 (04);1-47,51.

Recommendation of the Immunization Practices Advisory Committee (ACIP) Diphtheria, Tetanus, and Pertussis: Guidelines for Vaccine Prophylaxis and Other Preventive Measures. MMWR. 1985; 34(27);405-14,419-26.

Lee, WM. Hepatitis B Virus Infection. NEJM. 1997; 337(24): 1733-45.

Gringeri, et al. Anti-alpha-interferon (ifn-alpha) immunization—a 2-year follow-up of 44 HIV-infected patients. Aids Research and Human Retroviruses , 1995 , V 11 , S1 , p. S168.

Tanaka, et al. Immunotherapy of a vaccinia colon oncolysate prepared with interleukin-2 gene-encoded vaccinia virus and interferon-alpha increases the survival of mice bearing syngeneic colon adenocarcinoma. J. Immunother. 1994; 16(4):, 283-293.

Stickl et al. Dtsch. Med. Wochenschr. 1974; 99:2386-2392.

M. Franchini. et al., Dendritic Cells from Mice Neonatally Vaccinated with Modified Vaccinia Virus Ankara Transfer Resistance against Herpes Siimplex Virus Type Ito Naive One-Week-Old Mice. (2004) Journal of Immunology 172:6304-6312.

M. Franchini, et al., Protective T-Cell-Based Immunity Induced in Neonatal Mice by a Single Replicative Cycle of Herpes Simplex Virus. (2001) Journal of Virology 75:83-89.

S. Vollstedt. et al., Interleukin-12- and Gamma Interferon-Dependent Innate Immunity Are Essential and Sufficient for the Long-Term Survival of Passively Immunized Mice Infected with Herpes Simplex Virus Type 1. (2001) 75:9596-9600.

S. Vollstedt, et al., Flt3 ligand-treated neonatal mice have increased innate immunity against intracellular pathogens and efficiently control virus infection. (2003) J. Exp. Med V197:575-584.

Committee on Infectious Diseases and Committee on Fetus and Newborn. Revised Indications for the Use of Palivizumab and Respiratory Syncytial Virus Immune Globulin Intravenous for the Prevention of Respiratory Syncytial Virus InfectionsPediatrics, 2003. vol. 112 No. 6, p. 1442-1446.

Meyer et al., Mapping of deletions in the genome of the highly attenuated vaccinia virus MVA and their influence of virulence, Journal of General Virology 72:1031-1038 (1991).

Baxter A/G & Baxter Healthcare SA, Opposition to EP Patent No. 1335987, Response, Aug. 9, 2010.

EPO Opposition Division, Opposition to EP Patent No. 1335987, Preliminary Opinion, Oct. 8, 2009.

Bavarian Nordic NS, Opposition to EP Patent No. 1335987, Response, Aug. 9, 2010.

Okeke et al, Modified vaccinia virus Ankara multiplies in rat IEC-6 cells and limited production of mature virions occurs in other mammalian cell lines, J. Gen Virol. 87:21-27 (2006).

Earl et al Generation of Recombinant Vaccinia Viruses, Current Protocols in Molecular Biology 16.17.1-16.17.19 (1998).

Grund Intellectual Property Group, Opposition to EP Patent No. 1420822, Response, Aug. 6, 2010.

EPO Opposition Division, Opposition to EP Patent No. 1420822, Preliminary Opinion, Oct. 8, 2009.

Bavarian Nordic A/S, Opposition to EP Patent No. 1420822, Response, Aug. 6, 2010.

Drexler et al., Highly attenuated modified vaccinia virus Ankara replicates in baby hamster kidney cells, a potential host for virus propagation, but not in various human transformed and primary cells, Journal of General Virology (1998), 79, 347-352.

Oxford Biomedica PLC et al., Defendants' Answer to Plaintiff's First Amended Complaint and Counterclaims, Case No. 08cv1156-MMA (RBB), Jun. 1, 2009.

Bavarian Nordic A/S, Plaintiff's Answers to Defendants' Counterclaims, Case No. 08cv1156-MMA (RBB), Jun. 22, 2009.

Bavarian Nordic A/S, Plaintiff's Motion for Partial Summary Judgement on Inequitable Conduct, Case No. 08cv1156-MMA (RBB), Jan. 25, 2010.

Declaration of Theodore J. Folkman, Case No. 08cv1156-MMA (RBB), Jan. 25, 2010.

Suter et al., Modified vaccinia Ankara strains with identical coding sequences actually represent complex mixtures of viruses that determine the biological properties of each strain, Vaccine 27:7442-7450 (2009).

Opposition Division, EPO, Opposition to EP Patent No. 1420822, EPA Form 2906, Oct. 8, 2009.

Emergent Product Development Germany GMBH, Opposition to EP Patent No. 1420822, Reply Letter, Sep. 23, 2009.

Bavarian Nordic, Opposition to EP Patent No. 1420822, Patentee Response to Oppositions, Mar. 27, 2009.

Sanofi Pasteur, Opposition to EP Patent No. 1420822, Notice of Opposition, Apr. 11, 2008.

Emergent Product Development Germany GMBH, Opposition to EP Patent No. 1420822, Notice of Opposition, Apr. 8, 2008.

Dr. Elfriede Dworak of the Commercial Court of Vienna, Austria, Decision on Initial Matter, without prejudice, in Case 19Cg 25/06g, May 31, 2007.

Mayr & Mayr, Pesq. Vet. Bras. 19:91-98 (1999).

Mayr et al., Infection 3:6-14 (1975).

Mayr et al., J. Vet Med. B. 3681-99 (1989).

Mayr et al., Drug Res. 37:988-989 (1987).

Mayr et al., J. Vet Med. B. 33:321-339 (1986).

Dr. Paul Chaplin, ITC Testimony, ITC Investigation No. 337-TA-550, 447-706, May 10, 2006

Mayr, Swiss Vet.11:13-17 (1999).

Paul Luckern, ALJ, Order No. 5, ITC Investigation No. 337-TA-550, Jun. 29, 2007.

Bavarian Nordic, 1999 Annual Report, Mar. 14, 2000.

Bavarian Nordic, 2000 Annual Report, Mar. 6, 2001.

Oxford Biomedica (UK) LTD, Opposition to EP Patent No. 1335987, Additional Submissions, Dec. 7, 2009.

Bavarian Nordic, Opposition to EP Patent No. 1335987, Reply to Submissions, Jun. 18, 2008.

Oxford Biomedica (UK) LTD, Opposition to EP Patent No. 1335987, Reply to Patentee's Response, Jan. 28, 2008.

Emergent Product Development Germany GMBH, Opposition to EP Patent No. 1335987, Submission to Patentee's Observations, Mar. 12, 2008.

Bavarian Nordic, Opposition to EP Patent No. 1335987, Response to Oppositions, Aug. 1, 2007.

Emergent Product Development Germany GMBH, Opposition to EP Patent No. 1335987, Notice of Opposition, Sep. 28, 2006.

Virbac SA, Opposition to EP Patent No. 1335987, Notice of Opposition, Sep. 28, 2006.

Innogenetics NV, Opposition to EP Patent No. 1335987, Notice of Opposition, Sep. 27, 2006.

Oxford Biomedica (UK) LTD, Opposition to EP Patent No. 1335987, Notice of Opposition, Sep. 26, 2006.

Baxter AG, Opposition to EP Patent No. 1335987, Notice of Opposition, May 15, 2006.

Sanofi Pasteur Inc, Opposition to EP Patent No. 1335987, Notice of Opposition, Sep. 26, 2006.

Acambis PLC, Opposition to EP Patent No. 1335987, Notice of Opposition, May 15, 2006.

Vollstedt et al., Flt3 Ligand-treated Neonatal Mice Have Increased Innate Immunity Against Intracellular Pathogens and Efficiently Control Virus Infections, J. Exp. Med. 197:575-584 (2003).

Franchini et al, Dendritic Cells from Mice Neonatally Vaccinated with Modified Vaccinia Virus Ankara Transfer Resistance against Herpes Simplex Virus Type I to Naive One-Week-Old Mice1, J. Immunology 172: 6304-6312 (2004).

Sutter et al., Nonreplicating vaccinia vector efficiently expresses recombinant genes. P.N.A.S. 89:10847-10851, 1992.

Blanchard et al., Modified vaccinia virus Ankara undergoes limited replication in human cells and lacks several immunomodulatory proteins: implications for use as a human vaccine. J. Gen Virology 79:1159-1167, 1998.

Schiver et al., Replication-incompetent adenoviral vaccine vector elicits effective anti-immunodeficiency-virus immunity. Nature 415:331-335, 2002.

Drexler et al., Modified Vaccinia Virus Ankara for Delivery of Human Tyrosinase as Melanomaassociated Antigen: Induction of Tyrosinase- and Melanoma-specific Human Leukocyte Antigen A*0201-restricted Cytotoxic T Cells in Vitro and in Vivo. Cancer Research 59:4955-4963, 1999.

Jungherr et al., Proposed method and Evaluation of trhe Monkey Neurovirulence Test for Attenuated Poliovirus Vaccine, The Journal of Infectious Diseases, 108(3) (1961), 247-261.

Rubin et al., Neurovirulence safety testing of mumps vaccines—Historical perspective and current status, Vaccine 29 (2011), 2850-2855.

Zhang et al., A mouse-based assay for the preclinical neurovirulence assessment of vaccinia virus-based smallpox vaccines, Biologicals 38(2) (2010), 278-283.

Baldick et al., Characterization and Temporal Regulation of mRNAs Encoded by Vaccinia Virus Intermediate-Stage Genes, J. Virol. 67 (1993), 3515-3527.

Wood et al., Using next-generation sequencing for high resolution multiplex analysis of copy number variation from nanogram quantities of DNA from formalin-fixed paraffin-embedded specimens, Nucleic Acids Res. 38(14):e151 (published online Jun. 4, 2010).

The Jackson Laboratory, Description, Mouse Strain B6.CB17-Prkdcscid/SzJ, printed Apr. 27, 2010.

Spertzel et al., Response of Irradiated Mice to Live Virus (TC-83) Immunization, Infection and Immunity 11:481-487 (1975).

Declaration of Dr. Mark Suter, D103, Opposition to EP Patent No. 1335987, Aug. 16, 2011.

Declaration of Dr. Dennis Panicali, D109, Opposition to EP Patent No. 1335987, Aug. 10, 2011.

A. Gomez Yafal, Growth of TBC-MVA in mammalian cell lines, D108 Opposition to EP Patent No. 1420822, Aug. 10, 2011.

Materials Transfer Agreement Between NIH and Acambis, D99, Opposition to EP Patent No. 1420822, Sep. 2, 2002.

Therion, TBC-FPV growth at 24 or 48 hpi, D116, Opposition to EP Patent No. 1420822, Aug. 10, 2011.

Dr. Gerd Sutter, Curriculum Vitae, D102, Opposition to EP Patent No. 1335987, Sep. 1, 2010.

NIH Laboratory Notebook, D91, II. Hela Cells, Opposition to EP Patent No. 1420822, Aug. 10, 2011.

ECACC, Deposit Receipt for ECACC V00083008, D111, Opposition to EP Patent No. 1420822, Aug. 30, 2000.

ECACC, Notifications of Deposit, D138, Opposition to EP Patent No. 1420822, (2005).

Bavarian Nordic GMBH, Transfer Agreement concerning Deposit, D112, Opposition to EP Patent No. 1420822, Oct. 27, 2000.

ECACC, Amended Deposit Receipt for ECACC V00083008, D97, Opposition to EP Patent No. 1420822, May 1, 2005.

Taconic, Product information on "ICR scid" mice, D93, Opposition to EP Patent No. 1420822, Aug. 11, 2011.

Charles River, Technical Sheet, The CB17/lcr-Prkdcscid/IcrIcoCrl Mouse, D94, Opposition to EP Patent No. 1420822, (2009).

Bavarian Nordic A/S, Press release on arbitration with GSF, D95, Opposition to EP Patent No. 1420822, Apr. 20, 2011.

Bardehle, Press release on arbitration with GSF, D96, Opposition to EP Patent No. 1420822, Aug. 11, 2011.

Heritage Reporting Company, Hearing Transcript, D118, ITC Investigation No. 337-TA-550, May 10, 2006.

Bosma et al., The SCID mouse mutant: definition, characterization, and potential uses, Annu. rev. Immunol. 9:323-350 (1991).

Vossius & Partners, Observation of the Grounds of Appeal, D88, Opposition to EP Patent No. 1335987, Aug. 25, 2011.

Bosma et al., Evidence of Functional Lymphocytes in Some (Leaky) scid Mice, J. Exp. Med. 167:1016-1035 (1988).

Emergent Product Development Germany GMBH, MVA Sequence analysis using Illumina sequencing technology, D67, Opposition to EP 1420822, Apr. 11, 2011.

Abbas et al., D83, Cellular and Molecular Immunology, 5th Edn 2005, Elsevier, pp. 149, 441.

Declaration of Dr. Chris Upton, D68, Opposition to EP 1420822, Apr. 8, 2011.

Baxter'S Experimental Report MVA0015E01, "Replication studies of modified Vaccinia Ankara (MVA) strains in adult SCID mice" D78, Opposition to EP 1420822, Mar. 31, 2011.

Taconic, 'Leakiness' in C.B-17 SCID vs. ICR SCID, D82, Opposition to EP 1420822, Apr. 12, 2011.

Declaration of Dr. Karl Heller, D81, Opposition to EP 1420822, Apr. 15, 2011.

Declaration of Dr. Georg Holzer, D80, Opposition to EP 1420822, Apr. 15, 2011.

Baxter's Experimental Report MVA001401, "Replication studies of modified Vaccinia Ankara (MVA) strains in suckling SCID mice" D79, Opposition to EP 1420822, Mar. 31, 2011.

Yeadon, Email from Jackson Laboratory concerning AGR129 mice, D73, Opposition to EP 1420822, Apr. 1, 2011.

Jackson Laboratory, Extracts from the concerning mouse strains NOD-scid IL2R-gamma null and NOD Rag1 perforin mutant mice, D85, Opposition to EP 1420822, Mar. 31, 2011.

Second Declaration of Dr. Bertram Jacobs, Opposition to EP 1420822, Apr. 8, 2011.

Carroll et al., T Cell Leakiness in Scid Mice, Curr. Top. Microbiol. Immunol 152, 117-123 (1989).

Abbas et al., Cellular and Molecular Immunology, D72, 6th edition 2009, Saunders, pp. 93.

Wright et al., Beyond the Consensus: Dissecting Within-Host Viral Population Diversity of Foot-and-Mouth Disease Virus by Using Next-Generation Genome Sequencing, J. Virology 85 (5), 2266-2275 (2011).

Drexler et al., Identification of vaccinia virus epitope-specific HLA-A*0201-restricted T cells and comparative analysis of smallpox vaccines, Proc. Natl. Acad. Sci. USA 100, 217-222 (2003).

Potter Clarkson, Grounds of Appeal, D77, Opposition to EP 1335987, Apr. 15, 2011.

Grund, Grounds of Appeal, D74, Opposition to EP 1335987, Apr. 11, 2011.

Grund, Grounds of Appeal, Opposition to EP 1420822, Apr. 11, 2011.

Grund, Grounds of Appeal, Opposition to EP 1420822, May 5, 2011.

Vossius & Partners, Observation on the Grounds of Appeal, Opposition to EP Patent No. 1420822, Aug. 25, 2011.

Grund, Reply to Grounds of Appeal, Opposition to EP 1420822, Aug. 24, 2011.

Vossius & Partners, Grounds of Appeal, Opposition to EP Patent No. 1420822, Apr. 11, 2011.

EPO Opposition Division, Interlocutory Decision, Opposition to EP Patent No. 1420822, Nov. 17, 2011.

Sutter et al., Nonreplicating vaccinia vector efficiently expresses recombinant genes, PNAS 89:10847-10851 (1992).

* cited by examiner

Figure 2:

CD11c cells in 2 w old mice after MVA treatment

| Experiment BN9 | | blood | | spleen | |
|---|---|---|---|---|---|
| | n | % CD11c | % CD11c CD8 | % CD11c | % CD11c CD8 |
| naïve | 3 | 3.5 | 0.4 | 4.9 | 1.3 |
| 1 Vaccination at birth | 3 | 7.4 | 2.1 | 16.1 | 2.0 |
| 1 vaccination at d7 | 4 | 21.5 | 17.0 | 4.4 | 17.6 |
| 2 vaccination d 0 and 7 | 4 | 42.7 | 35.6 | 27.9 | 25.7 |

Figure 5:

9 challenge experiments with HSV-1

|          | infected | survivors |
|----------|----------|-----------|
| Controls | 45       | 0         |
| MVA      | 40       | 34        |

MODIFIED VACCINIA VIRUS ANKARA FOR THE VACCINATION OF NEONATES

This application is a continuation application of application Ser. No. 12/607,585, filed Oct. 28, 2009, which is a continuation application of application Ser. No. 11/112,438, filed Apr. 22, 2005, now U.S. Pat. No. 7,628,980, which is a continuation-in-part of application Ser. No. 10/418,854, filed Apr. 18, 2003, now U.S. Pat. No. 7,097,842, which is a continuation-in-part of Application No. PCT/EP01/13628, filed on Nov. 22, 2001, all of which are incorporated by reference.

The invention concerns the use of a virus for the preparation of a medicament for the vaccination or treatment of a neonatal or prenatal animal, including a human, wherein the virus is capable of infecting the cells of the neonatal or prenatal animal, including a human, but not capable of being replicated to infectious progeny virus in the neonatal or prenatal animal, including a human. The virus may be a Modified Vaccinia Virus Ankara.

In particular, the invention concerns the vaccination of neonates against infections with viruses belonging to the same virus group as the virus used for vaccination. Moreover, the invention concerns the vaccination of neonates against antigens selected from foreign antigens and tumour antigens, wherein the tumour antigen and/or the foreign antigen are different from the antigens associated with the virus. The invention further concerns the use of viruses as defined above to increase the level of factors which activate dendritic cells or their precursor cells and/or to increase the number of dendritic cells or their precursor cells and/or to increase the production and/or cellular content of an interferon (IFN) or IL-12.

BACKGROUND OF THE INVENTION

The natural environment of animals and human beings contains a large variety of infectious agents such as viruses, bacteria or fungi. Many of these infectious agents may cause diseases in the infected hosts. Under normal circumstances the infected host recovers from the disease induced by the infectious agent after a certain period of time. This recovery is due to the immune system of an animal or a human being.

The immune system is the part of a human or animal body that is responsible for eliminating the infectious agent. The immune response is divided into a specific and an unspecific (innate) reaction although both cooperate closely. The unspecific immune response is the immediate defense against a wide variety of foreign substances and infectious agents. In the innate immune response against viruses, Interferon (IFN)-α and IFN-β are absolutely essential to control the initial virus replication and to activate natural killer (NK) cells for immediate killing of infected cells. Intracellular bacterial or parasitic pathogens induce IL-12 that up regulates IFN-γ in NK cells and/or some T cell subsets. IFN-γ activated NK cells can now kill intracellular pathogens. Moreover, IFN-γ also activates macrophages and enables them to kill internalized pathogens.

By far the richest source of IFN-α/β, on a per cell basis, are dendritic cells (DC), a specialized cell population strategically distributed throughout the body. Plasmacytoid DC or $CD11c^+ CD8^+$ DC are among the best producers of IFN-α/β. $CD8^+$ DC that are infected with intracellular non-viral pathogens are the crucial cells able to secrete IL-12 essential for the early steps in immune defense.

A specific immune response can be induced against a particular foreign substance (antigen) after a lag phase, when the organism is challenged with this substance for the first time. The initiation of the specific immune response is coordinated by DC, too. There is a constant traffic of these cells from the periphery to the secondary lymphoid organs, the lymph nodes or spleen where naïve T and B cells recirculate. Antigen that is carried by DC to these organs, enables activation of naïve T- and B cells to become effector T- and B cells. For this, DC's not only carry the antigen, but the plasticity of pathogen recognition allows different gene activation in DC and thus a pathogen adjusted priming of T cells.

The specific immune response is highly efficient and is responsible for the fact that an individual who recovers from a specific infection is protected against this specific infection. Thus, a second infection with the same or a very similar infectious agent causes much milder symptoms or no symptoms at all, since there is already a "pre-existing specific immunity" to this agent. Such immunity and the immunological memory, respectively, persist for a long time, in some cases even lifelong. Accordingly, the induction of an immunological memory can be used for vaccination, i.e. to protect an individual against infection with a specific pathogen.

For vaccination the immune system is challenged with a vaccine which itself is less harmful than the pathogenic agent against which an immune response is to be induced. The vaccine comprises or expresses epitopes that are found in or expressed by the agent against which the vaccination is done. The organism, thus, is immunized against the agent containing the epitope that is part of the vaccine.

Typical vaccines are attenuated or inactivated viruses (e.g. the polio or small poxvirus vaccines), recombinant proteins (e.g. recombinant Hepatitis B virus S-protein), heat inactivated bacterial toxins (*Clostridium tetani* toxin) or polysaccharides of the bacterial capsule wall (*Streptococcus pneumoniae*).

Since infectious diseases might lead to very critical conditions in newborns and nursing infants, there is an interest to vaccinate children or newborn animals as early as possible. Examples for conditions against which a vaccination is desirable are poxvirus infections, including smallpox. However, the attempts to successfully vaccinate newborns are hampered by the fact that the immune system of newborn mammals is not yet mature. The immune system of neonatal infants and mammalian animals is thought to mature gradually over a certain period of time. For humans the maturation occurs during the first year of life. This is the reason for the fact that the neonatal age group is left open to various infections during this first year (Gans et al., J. Am. Med. Assoc. (1998) 280, 527-532). More particularly, the neonatal infants have impaired B-cell function, deficiencies in primary antigen presentation by dendritic cells and limited T-cell proliferation (Gans et al., J. Am. Med. Assoc. (1998) 280, 527-532). Shortly after birth the levels of T cells in the spleen are 1,000 fold lower than in adults. In order to achieve at least a weak immunization it was suggested to use either replicating viruses or formulations comprising an adjuvant for immunization. However, with replication viruses there is always the risk that the immature immune system may become overwhelmed by virus infection or live viral vaccines since T cells are necessary for viral clearance (Hassett et al., J. Virol. (1997) 71, 7881-7888). Since there is a reduced production of cytokines by Th-1 helper T cells in neonates, the response by the infants is predominantly Th-2. Consequently, cytotoxic T cells are not recruited and viral clearance is not achieved.

The situation in mammalian animals is very similar to the situation in humans, i.e. the immune system after birth is not yet mature. In newborn mice, the number of splenic CD4+ T cells and CD8+ T cells is, respectively, 80,000-fold and 1000- fold lower than in spleens of adults. Moreover, the Interferon (IFN) producing system is immature in these mice. Therefore, neonatal mice are unable to efficiently control the expansion of intracellular pathogens by IFN at the site of infection. In addition, the low number and possibly inadequate activation stage of immune cells are too limited to cope with the rapidly expanding pathogens or replicating viruses used for vaccination.

Due to the risk associated with live viral vaccines, it is not recommended to vaccinate neonatal animals, including humans, with replicating viruses. E.g. it is recommended not to vaccinate newborns against smallpox with the vaccinia virus strains that have been used until the eradication of smallpox, such as strains Elstree, Copenhagen and NYCBH. According to recent recommendations in the USA, babies younger than 12 months of age should not get the smallpox vaccines commercialized so far.

The vaccination of neonates with formulations comprising an adjuvant has the disadvantage that numerous harmful substances are introduced into the body. Thus, a vaccination in human neonates is only done in emergency cases, e.g. in case of the Hepatitis B virus infection.

In summary, it is to be noted that the immune system is not mature at birth. Since the vaccination with replication competent viruses, or formulations comprising an adjuvant have significant disadvantages, infants are not vaccinated before the age of 2 months in Germany (Empfehlung der Ständigen Impfkommission STICO, 2001) or 6 weeks in the USA (ACIP "Recommended Childhood Immunization Schedule, United States").

The delay in the development of the immune system is compensated in part by the transfer of maternal antibodies from the mother to the nursing infant during pregnancy or by breastfeeding. However, not all infants are breastfed for various reasons. Thus, there is a very critical period of time of about 6-8 weeks in humans during which the infant having an immature and thus a not fully functional immune system does not receive maternal antibodies and during which a vaccination is usually not successful or too dangerous.

The situation is very similar in mammalian animals, in particular for economically important animals such as cows or companion animals such as cats and dogs. To reduce costs, the amount of milk the calf receives from the mother is often drastically reduced. Instead, the calf receives a mixture of milk powder, starter and specific concentrated feed, sometimes already in the first week after birth. Consequently, the calf does not receive the necessary amount and variety of maternal antibodies, so the immature immune system is very susceptible to infections. Furthermore, farmers who breed calves and those who raise them for meat production are often not the same. At 4 to 6 weeks of age calves from different breeder farms are pooled and shipped to other farms for meat production. At this time, when maternal antibodies are low and the immune system is not fully developed, the animals are exposed to new infectious agents under stress conditions. This increases the risk for infections that could be prevented by vaccination. A similar situation can be found in cat or dog breeding facilities where the risk for infection is high.

OBJECT OF THE INVENTION

It is the object of the present invention to provide a means to vaccinate newborn humans and animals, respectively, against foreign antigens and antigens that are associated with diseases in each group, respectively. More particularly, it is the object of the present invention to provide a means allowing the accelerated maturation of the immune system of newborn animals and humans. It is a further object of the present invention to provide a means that allows vaccinating neonatal animals, including humans, against poxvirus infections, in particular against smallpox.

SUMMARY OF THE INVENTION

What we therefore believe to be comprised by our invention may be summarized inter alia in the following words:

A method for inducing a long-term protection in an animal, including a human, against foreign antigens and tumor antigens, comprising the step of administering to the animal, including a human, at least one factor selected from type I interferons and Flt-3; such a method wherein the type I Interferon is an Interferon-alpha, or a derivative thereof, or an interferon-beta, or a derivative thereof; such a method wherein two or more of the factors are administered to the animal; such a method wherein the long-term protection lasts at least 5 days after the administration of the factor(s); such a method wherein the foreign antigen is an infectious agent; such a method wherein the infectious agent is selected from a virus, a bacterium, a prion, a parasitic agent, a eukaryotic unicellular or multicellular infectious agent and a fungus; such a method wherein the animal is a neonatal or prenatal animal; such a method wherein the animal is an adult animal; such a method wherein the animal is immune compromised; such a method wherein before, after or simultaneous to the administration of the factor, a virus is administered to the animal, wherein the virus is capable of infecting the cells of the animal but not capable of being replicated in these cells to infectious progeny virus; such a method wherein the virus is a DNA virus; such a method wherein the DNA-virus is selected from DISC-Herpes virus and Modified Vaccinia virus Ankara (MVA); such a method wherein the MVA virus is MVA-BN, deposited at the European Collection of Animal Cell Cultures (ECACC) with the deposition number V00083008, and derivatives thereof; such a method wherein the virus genome comprises at least one heterologous nucleic acid; such a method wherein the animal is a human; such a pharmaceutical composition for administration to an animal, including a human, which is designed to protect against foreign antigens and/or tumor antigens, comprising either (i) one or more factors, selected from type I interferons and Flt-3 and, optionally, a virus which is capable of infecting the cells of an animal, including a human, but not capable of being replicated in such cells to infectious virus progeny, or (ii) two or more factors selected from type I interferon and Flt-3 and, optionally, a virus which is capable of infecting the cells of an animal, including a human, but not capable of being replicated in such cells to infectious virus progeny; such a kit comprising the either (i) one or more factors, selected from type I interferons and Flt-3 and a virus which is capable of infecting the cells of an animal, including a human, but not capable of being replicated in such cells to infectious virus progeny or (ii) two or more factors selected from type I interferon and Flt-3 and, optionally, a virus which is capable of infecting the cells of an animal, including a human, but not capable of being replicated in such cells to infectious virus progeny; such a method for inducing an increase of the number of dendritic cells in an animal, including a human, comprising the step of administering to the animal, including a human, a factor selected from type I interferon and Flt-3; such a method wherein the dendritic cells (DC) may be conventional DC (cDC) and plasmacytoid pre DC (pDC); such a method wherein the type I Interferon is Interferon-alpha or interferon-beta; such a method wherein two or more of the factors are administered to the animal; such a method wherein the number of DC is increased for at least 5 days after the administration of the factor(s); such a method wherein the animal is a neonatal or prenatal animal; such a method wherein the animal is an adult animal; such a method wherein the animal is immune compromised; such a method wherein before, after or simultaneous to the administration of the factor, a virus is administered to the animal, wherein the virus is capable of infecting the cells of the animal but not capable of being replicated in these cells to infectious progeny virus; such a method wherein the virus is a DNA virus; such a method wherein the DNA-virus is selected from DISC-Herpesvirus and Modified Vaccinia virus Ankara (MVA); such a method wherein the MVA virus is MVA-BN, deposited at the European Collection of Animal Cell Cultures (ECACC) with the deposition number V00083008, and derivatives thereof; such a method wherein the virus genome comprises at least one heterologous nucleic acid; such a method wherein the animal is a human; such a method of inducing or enhancing the maturation and/or for the activation of the immune system of an animal, including a human, comprising the step of administering to the animal, including a human, a factor selected from type I interferon and Flt-3; such a method wherein the type I Interferon is Interferon-alpha or interferon-beta; such a method wherein two or more of the factors are administered to the animal; such a method wherein the animal is a neonatal or prenatal animal; such a method wherein the animal the immune system of which is to be activated is an adult animal; such a method wherein the animal is immune compromised; such a method wherein before, after or simultaneous to the administration of the factor, a virus is administered to the animal, wherein the virus is capable of infecting the cells of the animal but not capable of being replicated in these cells to infectious progeny virus; such a method wherein the virus is a DNA virus; such a method wherein the DNA-virus is selected from DISC-Herpesvirus and Modified Vaccinia virus Ankara (MVA); such a method wherein the MVA virus is MVA-BN, deposited at the European Collection of Animal Cell Cultures (ECACC) with the deposition number V00083008, and derivatives thereof; such a method wherein the virus genome comprises at least one heterologous nucleic acid; such a method wherein the animal is a human.

DETAILED DESCRIPTION OF THE INVENTION

According to the present invention it was unexpectedly found that it is possible to safely and efficiently vaccinate and/or treat neonatal or prenatal animals, including humans, with viruses that are capable of infecting cells of the neonatal or prenatal animal, including a human, but not capable of being replicated in said cells to infectious progeny virus. In particular it has been shown that the viruses used according to the present invention, such as MVA, in particular MVA-BN and its derivatives (see below), can be administered to newborns without showing any harmful effects. The vaccination of the animal with the virus leads to a specific immune response against the virus used for vaccination and/or to a general vaccination against foreign antigens and tumor antigens as explained below in more detail. Moreover, the viruses used according to the present invention lead to an induction and/or enhancement of the maturation of the immune system, which is associated with an increase in the number of dendritic cells and factors such as Interferons. Vaccination with the viruses used according to the present invention is possible even if the formulation administered to the animal does not comprise an adjuvant.

In summary, the viruses that are used according to the present invention (i) elicit an effective immune response in neonates, (ii) can be administered without the need of an adjuvant and (iii) do not bear the risk of overwhelming the organism.

According to the present invention the protective effect is exerted for at least 5 days, e.g. for at least 7, 14 or 28 days after the first vaccination.

Viruses that are "capable of infecting cells" are viruses harboring viral surface structures capable of interacting with the host cells to such an extent that the virus or at least the viral genome becomes incorporated into the host cell. Although the viruses used according to the present invention are capable of infecting the host cell, they are not capable of being replicated to infectious progeny virus in the infected cells. In the context of the present invention the term "virus not capable of being replicated to infectious progeny virus in said cells" refers to viruses the genome of which is at least partially transcribed and translated into viral proteins or even replicated, however, not packaged into infectious viral particles. Thus, the viruses used according to the present invention are viruses leading to abortive infections in the host. Abortive infections may occur for two reasons: according to the first alternative a cell may be susceptible to infection but it may be nonpermissive for multiplication of the virus; e.g. due to the fact that not all necessary viral genes for multiplication of the virus in said cell are expressed and/or present in the viral genome. An example of this type of virus according to the present invention in human cells is Modified Vaccinia Virus Ankara (MVA), which is explained in more detail below. According to the second alternative an abortive infection may also result from infection of cells with defective viruses, which lack a full complement of viral genes. An example of such a virus according to the present invention in human cells is DISC-HSV1 (disabled single-cycle Herpes simplex virus), i.e. a Herpes simplex virus, which is restricted to a single cycle of infection (Dilloo et al., Blood 1997, 89: 119-127). This virus lacks the gene for the essential glycoprotein H (gH), but can be grown to high titer in a complementing cell line expressing gH. In non-complementing cell lines that are permissive for herpes virus growth, it is restricted to a single cycle of replication, leading to the release of noninfectious virus. The term "not capable of being replicated" may refer to viruses that do not replicate in the cells of the vaccinated animal. However, viruses showing a minor residual replication activity that is controlled by the immature immune system of the neonate are within the scope of the present application.

The virus according to the present invention may be any virus that is capable of infecting cells of the animal, but not capable of being replicated to infectious progeny virus in said cells. It is to be understood, that a virus capable of infecting cells of a first animal species but not capable of being replicated to infectious progeny virus in said cells may behave differently in a second animal species. In humans for example, MVA-BN virus and its derivatives (see below) are capable of infecting cells, but are not capable of being replicated to infectious progeny virus in said human cells. The same viruses, however, are very efficiently replicated in chickens, i.e. MVA-BN virus is capable of infecting chicken cells, and replicating to infectious progeny virus in chicken cells. One skilled in the art understands which virus to choose for a specific animal species. U.S. Pat. No. 6,761,893 discloses a test using murine strain AGR129, that allows determination of whether a virus is capable, or not, of being replicated in a neonatal or prenatal animal. The results obtained in this murine model are indicative for humans. Thus, the term "not capable of being replicated to infectious progeny virus" as used in the present application corresponds to the term "failure to replicate in vivo" as used for mice in U.S. Pat. No. 6,761,893. More details on this test are given below. The viruses according to the present invention are preferably capable of being replicated in at least one type of cells of at least one animal species. Thus, it is possible to amplify the virus prior to administration to the animal that is to be vaccinated and/or treated. By way of example reference is made to MVA-BN that can be amplified in chicken embryo fibroblast (CEF) cells, but is not capable of being replicated to infectious progeny virus in the neonatal or prenatal human. In this context it is to be noted that chemically or physically inactivated viruses do not have all the properties of this embodiment. Inactivated viruses are capable of infecting the cells of the neonatal or prenatal animal, including a human and not capable of being replicated to infectious progeny virus in the neonatal or prenatal animal, including a human. However, inactivated viruses are not capable of replicating in at least one type of cells of at least one animal species.

The virus may be a DNA virus. For mammalian cells, in particular for human cells, the DNA virus may be selected from DISC-Herpesviruses and Modified Vaccinia virus Ankara (MVA).

Modified Vaccinia Ankara (MVA) virus is related to Vaccinia virus, a member of the genera Orthopoxvirus in the family of Poxviridae. MVA has been generated by 516 serial passages of the Ankara strain of vaccinia virus (CVA) (for review see Mayr, A., et al. Infection 3, 6-14 [1975]) in CEF. As a consequence of these long-term passages the resulting MVA virus deleted about 31 kilobases of its genomic sequence and, therefore, was described as highly host cell restricted to avian cells (Meyer, H. et al., J. Gen. Virol. 72, 1031-1038 [1991]). It was shown, in a variety of animal models that the resulting MVA was significantly avirulent (Mayr, A. & Danner, K. [1978] Dev. Biol. Stand. 41: 225-34). Additionally, this MVA strain has been tested in clinical trials as vaccine to immunize against a human smallpox disease (Mayr et al., Zbl. Bakt. Hyg. I, Abt. Org. B 167, 375-390 [1987], Stickl et al., Dtsch. med. Wschr. 99, 2386-2392 [1974]). These studies involved over 120,000 humans, including high risk patients, and proved that, compared to Vaccinia based vaccines, MVA had diminished virulence or infectiousness while it maintained good induction of immunity.

Examples of strains according to the present invention are MVA 575, deposited at the European Collection of Animal Cell Cultures (ECACC, CAMR Porton Down, Salisbury, Wilshire, SP4 OJG, UK) with the deposition number V00120707 on Dec. 7, 2000, MVA-572 deposited at ECACC with the deposition number V94012707 on Dec. 7, 2000, and MVA-BN deposited at ECACC with the deposition number V000083008 on Aug. 30, 2000, and derivatives thereof, in particular if it is intended to vaccinate/treat humans. An example of a stain that may be used in humans is MVA-BN and its derivatives.

By way of example the properties of MVA strains, in particular the properties of strains that may be administered to humans, such as MVA-BN and its derivatives, can be summarized as follows:

(i) capability of reproductive replication in chicken embryo fibroblasts (CEF) and in Baby Hamster Kidney cells (BHK), but no capability of reproductive replication in the human cell line HaCaT, (ii) failure to replicate in vivo, (iii) induction of a higher level of immunity compared to the known strain MVA 575 (ECACC V00120707) in a lethal challenge model and/or (iv) induction of at least substantially the same level of immunity in vaccinia virus prime/vaccinia virus boost regimes when compared to DNA-prime/vaccinia virus boost regimes.

MVA strains according to the present invention may possess property (ii) above, i.e., failure to replicate in the organism, which is to be vaccinated or treated and/or in the corresponding test system as explained below, and optionally, one additional of the above properties. The MVA strains may have three of the above properties. An example of an MVA strain having all of the above properties in humans is MVA-BN. Derivatives of MVA-BN may be derivatives having in addition to feature (ii), at least one additional of the above properties, at least two additional of the above properties, or all of the above properties.

Reference is made to U.S. Pat. No. 6,761,893 for detailed information regarding assays used to determine whether a MVA strain has one, or more, of the above features (i) to (iv). The publication also discloses how viruses having the desired properties can be obtained. In particular, U.S. Pat. No. 6,761,893 provides: a detailed definition of the features of MVA-BN and a derivative thereof; a detailed description of biological assays used to determine whether an MVA strain is MVA-BN or a derivative thereof; and methods to obtain MVA-BN or a derivative thereof. In other words, the features of MVA-BN; the description of biological assays allowing to evaluate whether a MVA strain is MVA-BN or a derivative thereof; and methods describing how to obtain MVA-BN, or a derivative thereof, are disclosed in U.S. Pat. No. 6,761,893.

The procedures disclosed in U.S. Pat. No. 6,761,893 are summarized below. This summary does not limit the relevance of this disclosure, the full extent of which is incorporated by reference.

The term "not capable of reproductive replication" in the cell line HaCaT (Boukamp et al. 1988, J Cell Biol 106(3): 761-71) is used in the present application as defined in U.S. Pat. No. 6,761,893. Thus, a virus that is "not capable of reproductive replication" in the cell line HaCaT is a virus that shows an amplification ratio of less than 1 in the human cell line HaCaT. The amplification rate of the virus used as a vector according to the invention may be 0.8 or less in the human cell line HaCaT. The "amplification ratio" of a virus is the ratio of virus produced from an infected cell (Output) to the amount originally used to infect the cells in the first place (Input) ("amplification ratio"). A ratio of "1" between Output and Input defines an amplification status wherein the amount of virus produced from the infected cells is the same as the amount initially used to infect the cells. The term "derivatives" of the viruses as deposited under ECACC V00083008 may refer to viruses showing essentially the same replication characteristics as the deposited strain but showing differences in one, or more parts, of its genome. Viruses having the same "replication characteristics" as the deposited virus replicate with similar amplification ratios as the deposited strain in CEF cells and the cell lines BHK, HeLa, HaCaT and 143B. These viruses also show a similar replication in vivo, as determined in the AGR129 transgenic mouse model (see below).

The term "failure to replicate in vivo" is used in the present application as defined in U.S. Pat. No. 6,761,893. Thus, the term refers to viruses that do not replicate in humans and in the murine model, as explained in U.S. Pat. No. 6,761,893. The mice used in U.S. Pat. No. 6,761,893 are incapable of producing mature B- and T-cells (AGR 129 mice). In particular, MVA-BN and its derivatives, do not kill AGR129 mice within mean (average) time periods of at least 45 days, or even of at least 60 days or even of at least 90 days after the infection of the mice with $10^7$ pfu virus administered intraperitoneally. The viruses that show "failure to replicate in vivo" are further characterized in that no virus can be recovered from organs or tissues of the AGR129 mice 45 days or 60 days or even 90 days (mean (average) values) after the infection of the mice with $10^7$ pfu virus administered intraperitoneally.

Instead of AGR129 mice, another mouse strain may be used which is incapable of producing mature B and T cells and, as such, is severely immune compromised and highly susceptible to a replicating virus.

The details of the lethal challenge experiment used to determine whether a MVA strain has "a higher immunogenicity compared to the known strain MVA 575" are explained in U.S. Pat. No. 6,761,893. In such a lethal challenge model unvaccinated mice die after the infection with replication competent vaccinia strains such as the Western Reserve strain L929 TK+ or IHD-J. The infection with replication competent vaccinia viruses is referred to as "challenge" in the context of description of the lethal challenge model. Four days after the challenge the mice are usually killed and the viral titer in the ovaries is determined by standard plaque assays using VERO cells. The viral titer is determined for unvaccinated mice and for mice vaccinated with MVA-BN and its derivatives. More specifically MVA-BN and its derivatives are characterized in that, in this test after the vaccination with $10^2$ TCID$_{50}$/ml virus the ovary virus titers are reduced by at least 70%, or by at least 80% or by even at least 90% (mean (average) values) compared to unvaccinated mice.

In a further embodiment the viruses according to the present invention, such as MVA, in particular MVA-BN and its derivatives, are useful for prime/boost administration. The viruses, in particular MVA strains such as MVA-BN and its derivatives, as well as, corresponding recombinant viruses harboring heterologous sequences, can be used to efficiently first prime, and then boost immune responses in naïve animals, as well as, in animals with a pre-existing immunity to poxviruses. Thus, the virus according to the present invention induces at least substantially the same level of immunity in vaccinia virus prime/vaccinia virus boost regimes compared to DNA-prime/vaccinia virus boost regimes.

A vaccinia virus, in particular an MVA strain, is regarded as inducing at least substantially the same level of immunity in vaccinia virus prime/vaccinia virus boost regimes when compared to DNA-prime/vaccinia virus boost regimes if the CTL response as measured in one of the "assay 1" and "assay 2" as disclosed in U.S. Pat. No. 6,761,893, or even in both assays, is at least substantially the same in vaccinia virus prime/vaccinia virus boost regimes when compared to DNA-prime/vaccinia virus boost regimes. The CTL response after vaccinia virus prime/vaccinia virus boost administration is higher in at least one of the assays, when compared to DNA-prime/vaccinia virus boost regimes. The CTL response may be higher in both assays.

The virus used according to the present invention may be a non-recombinant virus, such as MVA, i.e., a virus that does not contain heterologous nucleotide sequences. An example for a non-recombinant vaccinia virus is MVA-BN and its derivatives. Alternatively the virus may be a recombinant virus, such as a recombinant MVA that contains additional nucleotide sequences, which are heterologous to the virus.

The term "heterologous" as used in the present application refers to any combination of nucleic acid sequences that is not normally found intimately associated with the virus in nature; such virus is also called "recombinant virus".

The heterologous nucleic acid sequence may, for example, be selected from a sequence coding for at least one antigen, antigenic epitope, beneficial proteins and/or therapeutic compound.

The term "beneficial proteins" as used in the present application refers to any proteins that are helpful in protecting an animal against an antigen selected from tumor antigen and foreign antigen, wherein the tumor antigen and the foreign antigen is different from the antigens associated with the virus. Alternatively and more particularly the "beneficial proteins" are active in (i) increasing the level of factors which activate dendritic cells; and/or (i) increasing the number of dendritic cells; and/or (iii) increasing the production and/or cellular content of an interferon (IFN) or IL-12. Examples of such beneficial proteins are interferons, IL-12, Flt-3-L and or GM-CSF. Examples of interferons are type I interferons, such as IFN-alpha or IFN-beta.

The antigenic epitopes may be any epitope for which it is desired to induce an immune response. Examples for antigenic epitopes are epitopes from *Plasmodium falciparum*, Mycobacteria, Influenza virus, from viruses selected of the family of Flaviviruses, Paramyxoviruses, Hepatitis viruses, Human immunodeficiency viruses or from viruses causing hemorrhagic fever such as Hantaviruses or Filoviruses, i.e., Ebola or Marburg virus. Thus, if e.g. a recombinant MVA expressing heterologous epitopes is used to vaccinate neonates according to the present invention, the result of this treatment is not only a general vaccination due to the accelerated maturation of the immune system but also a specific vaccination against the heterologous epitope expressed from the heterologous MVA.

A "therapeutic compound" encoded by the heterologous nucleic acid in the recombinant virus can be, e.g., a therapeutic nucleic acid such as an antisense nucleic acid or a peptide or protein with desired biological activity.

The insertion of heterologous nucleic acid sequence may be done into a non-essential region of the virus genome. Alternatively, the heterologous nucleic acid sequence may be inserted at a naturally occurring deletion site of the viral genome (for MVA disclosed in PCT/EP96/02926). Methods how to insert heterologous sequences into the viral genome such as a poxviral genome are known to a person skilled in the art.

The present invention also provides a pharmaceutical composition and a vaccine comprising a virus according to the present invention, such as MVA, e.g., for inducing an immune response in a living animal body, including a human.

The pharmaceutical composition may generally include one or more pharmaceutical acceptable and/or approved carriers, additives, antibiotics, preservatives, adjuvants, diluents and/or stabilizers. Such auxiliary substances can be water, saline, glycerol, ethanol, wetting or emulsifying agents, pH buffering substances, or the like. Suitable carriers are typically large, slowly metabolized molecules such as proteins, polysaccharides, polylactic acids, polyglycollic acids, polymeric amino acids, amino acid copolymers, lipid aggregates, or the like.

For the preparation of vaccines, the virus or its recombinants is converted into a physiologically acceptable form. A person skilled in the art is familiar with such methods. For MVA and other poxviruses the vaccine can be prepared based on the experience in the preparation of poxvirus vaccines used for vaccination against smallpox (as described by Stickl, H. et al. [1974] Dtsch. med. Wschr. 99, 2386-2392). For example, the purified virus is stored at −80° C. with a titer of $5 \times 10^8$ $TCID_{50}$/ml formulated in about 10 mM Tris, 140 mM NaCl pH 7.4. For the preparation of vaccine shots, e.g., $10^1$-$10^8$ particles of the virus such as MVA are lyophilized in 100 ml of phosphate-buffered saline (PBS) in the presence of 2% peptone and 1% human albumin in an ampoule, such as a glass ampoule. Alternatively, the vaccine shots can be produced by stepwise freeze-drying of the virus in a formulation. This formulation can contain additional additives such as mannitol, dextran, sugar, glycine, lactose or polyvinylpyrrolidone or other additives such as antioxidants or inert gas, stabilizers or recombinant proteins (e.g. human serum albumin) suitable for in vivo administration. The glass ampoule is then sealed and can be stored between 4° C. and room temperature for several months. However, as long as no need exists, the ampoule may be stored at temperatures below −20° C.

For vaccination or therapy the lyophilisate can be dissolved in 0.1 to 0.5 ml of an aqueous solution, such as physiological saline or Tris buffer, and administered either systemically or locally, i.e., by parenteral, intramuscular or any other path of administration know to the skilled practitioner. The mode of administration, the dose, and the number of administrations, can be optimized by those skilled in the art in a known manner.

The virus according to the present invention, in particular MVA, can be administered by oral, nasal, intramuscular, intravenous, intraperitoneal, intradermal, intra-utero and/or subcutaneous application. In small animals the inoculation for immunization may be given by parenteral or nasal administration; whereas, in larger animals or humans, a subcutaneous, intramuscular or oral inoculation may be selected.

By way of example MVA may be administered in a dose of $10^1$ $TCID_{50}$ (tissue culture infectious dose) to $10^9$ $TCID_{50}$.

As indicated above, the virus according to the present invention, in particular MVA, such as MVA-BN and its derivatives may be administered in a therapeutically effective amount in a first inoculation ("priming inoculation") and in a second inoculation ("boosting inoculation").

In the context of the present invention the term "animal" also includes human beings. More generally, the animal is a vertebrate animal, such as a mammalian animal including a human. Specific examples of animals are pets, such as dogs and cats; economically important animals, such as calves, cattle, sheep, goats, horses, pigs; and other animal such as mice, rats. MVA and DISC-HSV are particularly preferred viruses for these animal species, and humans. The invention may also be used for economically important birds such as turkeys, ducks, goose and hens if the viruses used are capable of infecting avian cells, but not capable of being replicated to infectious progeny virus in said cells.

The term "domestic animals" as used in the present description refers inter alia to mammalian domestic animals, such as to dogs, cats, calves, cattle, sheep, goat, pigs, horses and deer.

According to a first alternative, the viruses according to the present invention, in particular MVA-BN and its derivatives may be used as specific vaccines, i.e. to elicit an immune response that protects the vaccinated newborn against diseases caused by a virulent virus belonging to the same virus group, family or genus than the virus that was used for vaccination. By way of example MVA as defined above, in particular MVA-BN and its derivatives can be used to vaccinate newborn humans against poxvirus infections, in particular against smallpox. MVA, in particular MVA-BN and its derivatives, may also be used to vaccinate vertebrate animals against poxvirus infections of veterinary importance. According to this first alternative the virus used for vaccination may be a non-recombinant virus, such as MVA-BN or its derivatives, or a recombinant virus harboring genes in the viral genome that are not naturally found in said genome. The recombinant virus may harbor additional genes that are helpful in stimulating the immune response. Examples for this kind of genes are cytokine genes and interferon genes.

According to a second, but related alternative, neonates are vaccinated with a recombinant virus harboring a heterologous nucleic acid sequence, as defined above, to induce an immune response against the amino acid sequence expressed from the heterologous nucleic acid sequence. By way of example the nucleic acid sequence may code for an antigen or an antigenic epitope, as defined above. Examples for a recombinant virus according to this embodiment are recombinant MVA, in particular recombinant MVA-BN or a derivative thereof, comprising a heterologous nucleic acid coding for antigens from (i) viruses other than MVA, such as HIV-1, HIV-2, Denguevirus, West-Nile Virus, Japanese Enchephalitis virus, measles virus, (ii) tumor antigens, (iii) bacteria, (iv) fungi. If the antigen expressed from the recombinant virus is, e.g., an HIV antigen it is possible to use the recombinant virus to induce an immune response in the vaccinated neonate against HIV and to prevent AIDS. In a broader sense the recombinant virus expressing the antigen or antigenic epitope is used to induce an immune response against the agent from which the heterologous sequence is derived and/or against the agent that comprises the antigen or antigenic epitope.

According to a third alternative, it has been unexpectedly found that viruses that are capable of infecting the cells of the neonatal or prenatal animal, including a human, but not capable of being replicated to infectious progeny virus in the neonatal or prenatal animal, including a human, can be used for the preparation of a medicament for protecting an animal, in particular a newborn animal, including a human, against an antigen selected from tumor antigens and foreign antigens, wherein the tumor antigen and/or the foreign antigen are different from the antigens associated with the virus.

According to this third alternative, newborns vaccinated with the viruses according to the present invention, in particular with MVA, such as MVA-BN and its derivatives, are protected against a challenge with foreign antigens such as infectious agents. Thus, the viruses according to the present invention, in particular MVA, are a general vaccine for newborns. That is, by vaccinating newborns with the viruses according to the present invention, in particular MVA, the immune system of the newborns becomes more competent to deal with foreign antigens such as viruses. In the Example section, this is exemplified for vaccination with MVA and a subsequent challenge with Herpes simplex virus type 1. Thus, if the virus according to the present invention, in particular MVA, is used for the vaccination of newborns the vaccinated animals are more protected against foreign antigens than unvaccinated animals during the critical time span until a functional and mature immune system is established.

According to the present invention "the tumor antigen and/or the foreign antigen is different from the antigens associated with virus". This term is to be interpreted, in that according to this embodiment, the invention is not primarily intended to use a virus, such as MVA, to induce an immune response against the virus itself. Instead, the virus is used to induce a immune response, or at least a general immune stimulation, that protects the host against foreign antigens and tumor antigens, respectively, that are not associated with the virus. The term "antigens associated with the virus" refers to epitopes and antigens of the virus particle, and to antigens and epitopes on the surface of a cell infected with the virus that are the result of the expression of the viral genome.

In the context of this embodiment the term "foreign antigens" refers to any antigens and epitopes that are not naturally a part, or a component, of the animal body. Foreign antigens are especially antigens and epitopes from infectious agents and toxins. Typical infectious agents are viruses such as herpesviruses, retroviruses, rabiesviruses, rhabdoviruses, adenoviruses; bacteria such as *Salmonella, Mycoplasm, Meningicoccus, Hemophilus*; prions or fungi.

The invention is not only of interest to vaccinate animals against foreign antigens but, in an alternative embodiment, is also suitable to vaccinate against tumor antigens. "Tumor antigens" are antigens associated with certain tumoral diseases. Tumor antigens are most often antigens encoded by the genome of the host that develops the tumor. Thus, in a strict sense tumor antigens are not foreign antigens. However, tumor antigens are found in significant amounts in tumors; whereas, the amount of tumor antigens in normal tissues is significantly lower, and most often no tumor antigens are found at all in normal tissue. Examples for tumor antigens are known to the person skilled in the art and include, e.g. the MAGE antigens. MVA is effective against these tumor antigens since the vaccination of an animal leads to an activation and/or accelerated maturation of the immune system which then may lead to the destruction of tumor cells.

The term "protecting against an antigen" refers to the development of an immune response, which is directed against the foreign or tumor antigen. If the foreign antigen is an infectious agent, the host is protected against the agent, i.e., the host develops an immune response against said antigen. Consequently, the infection with the infectious agent leads to a less severe disease or to no disease at all. The term "protecting" is not to be understood in the sense that there is always a 100% protection against the foreign or tumor antigen. Instead, the term "protection" as used in the present application refers to any beneficial effect that helps the animal to deal with the foreign antigen and the tumor antigen, respectively.

According to the present invention such a protective effect is exerted for at least 5 days, e.g., for at least 7, 14 or 28 days after the first vaccination. In other words, the vaccinated and/or treated animal is protected, e.g., against a foreign antigen if the animal comes into contact with said antigen after 5, 7, 14 and 28 days, respectively.

In the context of the present invention the effect of the vaccination of newborns with the virus according to the present invention, in particular with MVA may be explained by the induction or enhancement of maturation of the immune system and/or the activation of the immune system. In the context of the present invention, the term "induction or enhancement of the maturation of the immune system" refers inter alia to the accelerated increase of dendritic cells or their precursors in vaccinees relative to controls. The terms "acceleration of the maturation" of the immune system and "enhancement of the maturation" of the immune system are used interchangeably in this description.

The "activation of the immune system" is characterized by the secretion and/or cell surface expression of molecules and hormones that facilitate cell/cell interaction or trafficking. Specific receptors take up these signals and respond. Activation markers are inter alia Flt3-L, IL-12, IFN-alpha, MHC-11 and CD8, in particular CD8alpha (see below).

The accelerated development/maturation of the immune system is correlated with (i) an increase of the level of factors activating and or mobilizing dendritic cells (DC) or their precursor cells; and/or (ii) an increase in the number of dendritic cells and their precursor cells; and/or (iii) an increase in the production and/or cellular content of an interferon or IL-12. An example for DC precursor cells that are induced by the virus according to the present invention, in particular by MVA, are plasmacytoid DC precursors that are very important for the defense against viral infections and that seem to produce IFN $\alpha/\beta$.

More specifically, the enhancement of the maturation of the immune system may be defined by an at least 2-fold increase in surface markers found on DC, such as MHC-11, CD40 and/or CD80/86. Such an increase can be measured in the blood. Additional markers to characterize an enhancement of the maturation of the immune system are Flt3-L, IL-12, IFN-alpha, MHC-11 and CD8a (see below). Moreover, the accelerated maturation of the immune system may be correlated to an at least 1.5 fold increase, such as at least a 2.0-fold increase in the number of CD11c positive cells in the blood, and/or the spleen, 7 days after the administration of MVA-BN to newborn animals when compared to control animals that have not received MVA-BN. Moreover, the enhancement of maturation of the immune system may be correlated with at least a 1.5-fold increase, such as at least a 2.0-fold increase of the concentration of Flt3-L, two days after the vaccination of neonates with viruses according to the present invention, when compared to age matched controls.

In this context it is to be noted that there is an association between the phenotype and function of murine and human DC populations that can be characterized by their surface phenotype (Hochrein et al. 2002. *Hum. Immunol.* 63: 1103). Dendritic cells in the blood can be detected using flow cytometry using a range of surface markers (MacDonald et al. 2002. *Blood.* 100:4512) that also allow specific populations of DC, such as the plasmacytoid DC to be identified (Dzionek et al. 2002. *Hum Immunol.* 63: 1133; Dzionek et al 2000. *J. Immunol.* 165: 6037). Using similar techniques DC can also be detected in other human tissues (Summers et al. 2001. *Am. J. Pathol.* 159: 285).

According to the present invention the viruses as defined above might also be used to treat neonatal or prenatal animals to (i) increase the level of factors activating and or mobilizing dendritic cells (DC) or their precursor cells; and/or (ii) to increase in the number of dendritic cells and their precursor cells; and/or (iii) to increase in the production and/or cellular content of an interferon or IL-12. It has been demonstrated that following vaccination with MVA-BN the plasmacytoid dendritic cells upregulate MHC-11 and CD8a and produce significantly more IL-12 and IFN-alpha. The increase of IL-12 after the administration of the viruses used according to the present invention may be 2-fold, 100-fold, 500-fold, 1000-fold, 2500-fold or 5000-fold. The increase of the concentration of Flt3-L two days after the vaccination of neonates with viruses according to the present invention, such as MVA-BN or its derivatives, may be at least 1.5-fold, such as at least 2.0-fold when compared to age matched controls.

The term "activation of dendritic cells or their precursors" refers to the maturation of DC to antigen presenting cells through ill-defined cell stages driven by hormones and different antigenic stimuli. Intermediates of DC are termed precursors. These immature DC reach the periphery. Activation markers which are upregulated in activated dendritic cells are inter alia Flt3-L, IL-12, IFN-alpha, MHC-11 and CD8a (see below).

It was noted that hormones such as GM-CSF lead to more immature DC in the periphery. Because GM-CSF leads to more DC precursor in bone marrow, blood and peripheral organs (and the cells have to move there), this phenomenon has been termed "mobilization of dendritic cells or their precursors". This definition is also used in the present description.

Consequently, the vaccination of animals including a human is especially useful, if it is intended to (i) increase the level of factors activating dendritic cells (DC) or their precursor cells; and/or (ii) increase the number of dendritic cells or their precursor cells; and/or (iii) increase the production and/or cellular content of an interferon or IL-12.

Factors that activate dendritic cells include inter alia Flt3-L (Lyman et al., Cell 1993, 75: 1157-1167) and GM-CSF. Typical interferons according to the present invention are IFN-alpha and IFN-beta. The viruses used according to the present invention induce Flt3-L and it is assumed that some of the beneficial effects observed are due to said induction.

In the context of the present application a newborn animal, or human, is defined as an animal or human, not yet having a mature immune system. Throughout this specification the terms "newborn animal" and "neonatal animal" are used synonymously. A mature immune system is characterized by the ability to fully activate the innate immune system, and by the fact that all known T and B cell functions and products are in place; in particular immunoglobulin isotypes such as IgA and IgE. Thus an immature immune system is characterized by a low number of T cells, B cells and dendritic cells relative to adults; by low IFN production compared to adults; and by the fact that the secondary lymphoid organs are not fully mature. More specifically a "neonatal" or "newborn" in the context of the present invention may be defined as an infant animal having a number of splenic CD4+ cells being at least 2-fold, at least 20-fold, at least 200-fold, at least 2,000-fold, or even at least 20,000-fold lower than the average number of splenic CD4+ cells in adults.

In mice the immune system is mature at the age of 4 weeks. In humans maturity is probably 6 months to 1 year. In cats and dogs the immune system is mature usually at the age of 6 months; in calves, sheep and pigs at the age of 4-12 weeks. Vaccination with the virus according to the present invention, in particular with MVA, may be done during before the immune system is mature. However, since maturity develops almost exponentially after birth, it is possible to vaccinate with the virus according to the present invention, in particular with MVA, as early after birth as possible. Since in all relevant domestic animals, and in humans, the immune system is mature not earlier than 4 weeks after birth, the vaccination with the virus according to the present invention, in particular with MVA, is done within 4 weeks after birth, e.g., within 2 weeks after birth, within 1 week after birth or even within 3 days after birth. These general terms are applicable to all important domestic animals, in particular to all important domestic mammalian animals, including humans. The person skilled in the art will be aware of the fact that even older animals may be regarded as newborns/neonates in the context of the present invention; and therefore vaccination may also be successfully carried out with older animals, when the immune system is not yet mature 4 weeks after birth. Thus, in humans the vaccination may be carried out within 6 months after birth, e.g., within 3 months after birth, within 2 months after birth, within 4 weeks after birth, within 2 weeks after birth, within 1 week after birth or even within 3 days after birth.

Since the best effects of the virus according to the present invention, in particular MVA as a general vaccine are observed if the virus is administered to an immature immune system, it might be useful to vaccinate even prenatal animals including humans. Prenatal vaccination may be desirable in economically important animals such as cattle or pigs. If the placenta allows the passage of the virus, the prenate can be vaccinated simply by vaccinating the mother animal. Thus, the vaccination of the mother animal to vaccinate the prenate is particularly promising in an animal having a placenta endotheliochorialis, such as dogs, cats, rats and mice or having a placenta heamochorialis, such as primates including humans. In animals having a placenta chorionepithelialis, such as cattle and sheep or having a placenta syndesmochorialis, such as pigs and horses, the vaccination of prenates can be done by in utero administration. Of course, this mode of administration can be also done for animal having a placenta endotheliochorialis or haemochorialis.

Since the viruses according to the present invention, in particular MVA, lead to an accelerated maturation of the immune system and are, thus, useful as a general vaccine, the vaccinated animals are protected against a variety of diseases. More specifically the viruses according to the present invention, in particular MVA, can be used to vaccinate cats for general well being and against feline herpes or feline infectious peritonitis. The viruses according to the present invention, in particular MVA, may be used in dogs for general well being and against respiratory tract associated (viral) diseases. The viruses according to the present invention, in particular MVA, may be used in pigs for general well being and against *Hemophilus* or *Mycoplasm* infections, especially in fattening pigs.

As previously indicated, one may administer the viruses according to the present invention, in particular MVA, in newborns or prenatal animals to protect said animal against a foreign antigen and/or a tumor antigen, wherein the tumor antigen is different from the antigens associated with the virus used for vaccination. However this embodiment is not restricted to newborn and prenatal animals. Instead, in an alternative embodiment, the invention can be carried out for animals of all ages, since a beneficial effect can be observed also in adult animals. Thus, according to this embodiment the viruses as defined above, in particular MVA-BN and its derivatives, are useful to protect an animal, including a human, against an antigen selected from tumor antigen and foreign antigen, wherein the tumor antigen and/or the foreign antigen is different from the antigens associated with the virus. As indicated above, the viruses used according to the present invention are capable of infecting cells of the animal but not capable of being replicated to infectious progeny virus in said cells. All information, definitions, including the definition of the duration of the protective effect, also apply for the present embodiment according to which the virus may also be administered to adults.

In contrast to newborns, the immune system of adult animals has already matured. Nevertheless, it might be that the immune system is weakened due to certain diseases or simply due to the age of the animal. Especially in immune-compromised people and in elderly people, the administration of the viruses according to the present invention, in particular MVA, to the animal may have a beneficial effect inter alia by (i) increasing the level of factors activating and/or mobilizing dendritic cells (DC) or their precursor cells; and/or (ii) by increasing the number of dendritic cells or their precursor cells; and/or (iii) by increasing the production and/or cellular content of an interferon or IL-12. Thus, even in adult animals, the administration of the viruses according to the present invention, in particular MVA, may lead to an increased competence of the immune system to deal with foreign antigens and/or tumor antigens. In other words, the viruses used according to the present invention are useful for the activation of the immune system in general.

The invention further concerns the viruses according to the present invention, in particular MVA, for the preparation of a medicament to be administered to an animal, including a human, wherein said medicament (i) increases the level of factors which activate dendritic cells; and/or (ii) increases the number of dendritic cells; and/or (iii) increases the production and/or cellular content of an interferon (IFN) or IL-12. All definitions given above for the other embodiments are also applicable for the present embodiment. According to this embodiment the invention does not aim primarily at inducing a protection against foreign antigens and/or tumor antigens. Instead, this embodiment is aimed at treating conditions and diseases characterized by (i) a low level of factors which activate dendritic cells; and/or (ii) insufficient or too low number of dendritic cells; and/or (iii) low production and/or cellular content of an interferon (IFN) or IL-12. Thus, according to this embodiment the treatment with the viruses according to the present invention, in particular MVA could protect against allergies or autoimmune diseases. Again this treatment is particularly promising if the viruses according to the present invention, in particular MVA, are administered to newborn animals.

Additionally, according to a further embodiment the virus according to the present invention, such as MVA, in particular MVA-BN and its derivatives, is particularly useful to induce immune responses in immuno-compromised animals, e.g., monkeys (CD4<400/µl of blood) infected with SIV, or in immuno-compromised humans. The term "immuno-compromised" describes the status of the immune system of an individual, which shows only incomplete immune responses or has a reduced efficiency in the defense against infectious agents.

The invention further concerns a method for protecting an animal, including a human, against an antigen selected from tumor antigen and foreign antigen, by administration of a virus according to the present invention, in particular Modified Vaccinia virus Ankara (MVA), wherein the tumor antigen and/or the foreign antigen is different from the antigens associated with the virus.

In a further embodiment the invention concerns a method for the treatment of an animal, including a human, comprising the administration of a Modified Vaccinia virus Ankara (MVA) to (i) increase the level of factors which activate dendritic cells; and/or (ii) increase the number of dendritic cells; and/or (iii) increase the production and/or cellular content of an interferon (IFN) or IL-12.

According to an alternative embodiment of the present invention, one or more of the beneficial proteins as defined above, such as type I Interferon and/or Flt-3L may by administered to the animal instead of, or in addition to, the virus that is capable of infecting cells of the animal but not capable of being replicated to infectious progeny virus in the cells. The effect that is achieved by administering one or more of the beneficial proteins such as type I Interferon and/or Flt-3L, optionally in combination with the virus a defined above, is comparable to that achieved if the virus, as defined above, is administered alone. Thus, the effect may be (i) a long-term protection of the animal against foreign antigens and tumor antigens; and/or (ii) a long-term increase of the number of dendritic cells in the animal; and/or (iii) an induction or enhancement of the maturation of the immune system of the animal; and/or (iv) an activation of the immune system of the animal.

If not stated otherwise, all definitions given so far are also applicable for the alternative embodiment. In the absence of indications to the contrary, the term "animal" generally also covers humans, i.e., the animal may be a human.

According to one example of this embodiment, it is sufficient to administer to the animal, including a human, one or more of the beneficial proteins, and it is not necessary to administer to the animal, including a human, a virus that is capable of infecting cells of the animal but is not capable of being replicated to infectious progeny virus in the cells.

According to another example of this embodiment, it is possible to administer to the animal, including a human, one or more of the beneficial proteins together with a virus that is capable of infecting cells of the animal but not capable of being replicated to infectious progeny virus in the cells. The administration of one or more beneficial proteins and the virus may be made simultaneously or within a time interval, e.g., the beneficial protein(s) may be administered before or after the administration of the virus. The time interval may be any convenient interval that leads to a beneficial effect in the animal, including a human. By way of example, the time interval between the administration of the beneficial protein(s) and the virus may be in the range of 1 day-2 months, such as in a range of 2 days-1 month, or in a range of 3 days-2 weeks, or the time interval may, for example, be about 1 week. It is possible to first administer the beneficial protein(s) and then to administer the virus. Alternatively, it is also possible to first administer the virus and then to administer the beneficial protein(s). The virus used in this example of the alternative embodiment may be a DNA virus. The DNA virus may be a DISC-Herpesvirus or a Modified Vaccinia virus Ankara (MVA). The MVA strain may be MVA-BN, deposited at the European Collection of Animal Cell Cultures (ECACC) with the deposition number V00083008, and derivatives thereof. The virus may be a recombinant virus, the genome of which comprises at least one heterologous nucleic acid.

The type I interferon may be IFN-alpha or IFN-beta. Any IFN-alpha or -beta may be used. The term "IFN-alpha" includes naturally occurring IFN-alpha, recombinant IFN-alpha, synthetic IFN-alpha, consensus IFN-alpha, modified IFN-alpha and derivatives of IFN-alpha, as well as fusion proteins comprising an IFN-alpha moiety. The term "IFN-beta" includes naturally occurring IFN-beta, modified IFN-beta, recombinant IFN-beta and derivatives of IFN-beta, as well as fusion proteins comprising an IFN-beta moiety. Non-limiting examples of IFN which is non-species specific are recombinant hybrid interferon hIFN (Gehring et al., Journal of Medical Virology 2005, 75:249-257) and alpha 2a-IFN (Parez, N. et al, British Journal of Haematology, 2000, 110, 420-423).

The term "modified" Interferon relates to Interferons being modified with non-protein residues. Examples of modified IFN are PEG (polyethylene glycol) modified IFN (Gehring et al., Journal of Medical Virology 2005, 75:249-257; Pawlotsky, J.-M., N. Engl. J. Med. 2004, 351:422-423) or glycosylated IFN.

The term "derivative" of an Interferon relates to proteins in which one or more amino acids are deleted, substituted, modified or inserted with respect to known Interferon protein sequences. The Interferon derivatives according to the present invention may be derivatives that (i) still have the biological activity of inducing a long-term protection in an animal against foreign antigens and tumor antigens; and/or (ii) still have the biological activity of long-term increasing the number of dendritic cells; and/or (iii) still have the biological function of inducing or enhancing the maturation and/or activation of the immune system of an animal.

IFN is administered in concentrations that depend on the species to which it is to be administered and the kind of IFN. Typical standard concentrations are known to the person skilled in the art. IFN may be administered once. Alternatively, it is also possible to administer IFN several times, e.g., once a week for several weeks; or every 2 to 4 days for one to several weeks. By way of example and without being bound thereto, reference is made to the following administration schemes: Mice may be treated with hIFN ranging in concentration from $1\times10^3$ to $1\times10^5$ U/injection. Human PEG-IFN-alpha may be administered to mice in weekly doses of 0.1 to 10 µg. In humans, including infants, alpha2a-IFN may be administered, e.g., in a concentration of $1\text{-}3\times10^6$ per injection, e.g., 1 to 3 times a week. In humans, PEG-IFN may be administered in a weekly dose of about 180 µg per week (Marcellin, P. et al., N. Engl. J. Med. 2004, 351:1206-1217)

Detailed information regarding Flt-3L, derivatives of Flt-3L such as truncated forms, dosages and modes of administration are given in numerous documents known to the person skilled in the art, e.g., in U.S. Pat. No. 6,190,655. Flt-3L may be a recombinant Flt-3L and/or a modified Flt-3L, such as PEG (polyethylene glycol) modified Flt-3L.

The actual dosage of Flt-3L depends on the species to which it is to be administered. Flt-3L may be administered once. Alternatively, it is also possible to administer Flt-3L several times, in the same regimes described above for IFN.

It is possible to administer only one factor, selected from type I interferon and Flt-3L. Alternatively, it is also possible to add two or more type I interferons, such as IFN-alpha and IFN-beta, or to add one or more type I Interferons and Flt-3L.

The effect of protecting an animal, including a human, as well as, the effect of increasing the number of dendritic cells, is a long-term effect. The effect is exerted, for example, for at least 5 days, for at least 7 days, for at least 14 days or for at least 28 days after the administration of the one or more beneficial proteins, such as a type I Interferon and/or Flt-3L.

The term "foreign antigen" in the context of the use of the beneficial proteins, refers to any antigens and epitopes that are not naturally a part or a component of the animal body (see also the definition given above). The "foreign antigen" may be any infectious agent such as a bacterium, a prion, a parasitic agent, a eukaryotic unicellular or multicellular infectious agent, a fungus or a virus. The virus may be any virus, such as poxvirus, smallpox virus, herpes virus, retrovirus, HIV, measles virus, rubella virus, rhinovirus, yellow fever virus, dengue virus, hepatitis viruses A, B, or C, rabies virus, rhabdovirus or any other virus.

The term "tumor antigen" has been defined above.

The animal may be a neonatal or prenatal animal, as defined above, in particular if it is intended (i) to protect the animal against foreign antigens and tumor antigens; (ii) to increase of the number of dendritic cells in the animal; (iii) to induce or enhance the maturation of the immune system; and/or (iv) to activate the immune system of the animal.

The animal may also be an adult animal, in particular if is intended (i) to protect the animal against foreign antigens and tumor antigens; (ii) to increase of the number of dendritic cells in the animal; and/or (iii) to activate the immune system of the animal.

Thus, according to this embodiment, the method according the present invention is useful for animals, including humans, of all age groups, including adults and elderly people as far as humans are concerned.

The animal may also be an immune-compromised animal.

The invention further concerns one or more beneficial proteins, optionally in combination with a virus that is capable of infecting cells of the animal but not capable of being replicated to infectious progeny virus in the cells, which is administered for a general immune stimulation. Thus, by way of example, this embodiment refers to the administration of one or more of the beneficial proteins, such as type I Interferon and/or Flt-3L to an animal, including a human, to protect said animal, including a human, for at least 5 days against foreign antigens, such as viruses.

There are many circumstances under which this embodiment is of particular interest, e.g., the one or more beneficial proteins, optionally in combination with a virus that is capable of infecting cells of the animal but not capable of being replicated to infectious progeny virus in said cells, may be administered to protect humans against diseases for which no vaccine is available. The one or more beneficial proteins, optionally in combination with a virus that is capable of infecting cells of the animal but not capable of being replicated to infectious progeny virus in said cells, also can be administered to protect humans against infectious diseases if there is not enough time for a vaccine to induce a protective immune response. This can be the case if one has to travel immediately to a country in which infectious diseases are endemic.

As discussed previously, the alternative embodiment may relate inter alia to the administration of beneficial proteins as defined above, such as type I Interferon and/or Flt-3L, optionally in combination with a virus as defined above, for a long-term increase of the number of dendritic cells in the animal, including a human. The dendritic cells (DC) are selected from conventional DC (cDC) and plasmacytoid pre DC (pDC). Methods are known to the person skilled in the art as to how an increase in the number of dendritic cells can be determined and as to how cDC's can be distinguished from pDC's (see O'Keeffe, M. et al., J. Exp. Med. 2002, 196:1307-1319).

The invention further relates to a composition comprising a combination of two or more of the beneficial factors as defined above, e.g., IFN-alpha and IFN-beta; IFN-alpha and Flt-3L; IFN-beta and Flt-3L; IFN-alpha, IFN-beta and Flt-3L.

The invention further relates to a composition comprising a combination of one or more of the beneficial proteins, as defined above, and a virus that is capable of infecting cells of the animal but not capable of being replicated to infectious progeny virus in said cells, and which is administered to the animal, including a human. By way of example, such a combination may comprise: IFN-alpha and MVA-BN or a derivative thereof; IFN-beta and MVA-BN or a derivative thereof; Flt-3L and MVA-BN or a derivative thereof; IFN-alpha, Flt-3L and MVA-BN or a derivative thereof; IFN-beta, Flt-3L and MVA-BN or a derivative thereof; IFN-alpha, IFN-beta, Flt-3L and MVA-BN or a derivative thereof; or any other combination.

The invention further relates to a kit comprising (i) one or more factors as defined above and a virus as defined above or (ii) two or more factors as defined above and, optionally, a virus as defined above; wherein the kit comprises at least two vials, and wherein the vials comprise different factors, combinations of factors, and/or viruses. Thus, one vial may comprise IFN-alpha and a second vial comprises MVA-BN or a derivative thereof; one vial may comprise IFN-beta and a second vial comprises MVA-BN or a derivative thereof; one vial comprises Flt-3L and a second vial may comprise MVA-BN or a derivative thereof; one vial may comprise IFN-alpha, a second vial may comprise Flt-3L and a third vial may comprise MVA-BN or a derivative thereof; one vial may comprise IFN-beta, a second vial may comprise Flt-3L and a third vial may comprise MVA-BN or a derivative thereof; one vial may comprise IFN-alpha, a second vial may comprise IFN-beta, a third vial may comprise Flt-3L and a fourth vial may comprise MVA-BN or a derivative thereof; or any other combination. It is also within the scope of the invention, that one of the at least two vials comprises a combination of two or more factors as defined above; or a combination of one or more factors, as defined above, and a virus, as defined above, and wherein the second vial comprises only one factor or virus, as defined above, or a combination of factors and/or virus that is different from the combination in the first vial.

According to a further alternative embodiment, it is also possible to administer dendritic cells from an animal that was treated with a factor, as defined above, or a virus, as defined above, to another animal to protect the animal against foreign antigens and/or tumor antigens. The factor may be selected from type I Interferons and Flt-3L, and the virus may be a MVA strain, such as MVA-BN. All definitions, concentrations and combinations given above apply also to this further embodiment. The DC's may be CD11+ cells. Methods are known to the person skilled in the art as to how to obtain DC and CD11+ cells, respectively. The first animal may be an animal of any age group, e.g., a neonatal animal. The cells may be isolated 5 days, 7, 8, 14 or even 28 days after the administration of the one or more beneficial proteins, such as a type I Interferon and/or Flt-3L, and/or the virus, as defined above.

SHORT DESCRIPTION OF THE FIGURES

FIG. 1A: Newborn mice were injected once within 24-48 h of birth with $10^6$ p.f.u. of MVA or DISC HSV-1 or treated with physiological saline (NaCl) as controls. At 7 days of age, CD11c, a pan DC marker was used to determine these cells in peripheral blood by flow cytometry. The mean and standard deviation of 3 to 5 experiments are shown.

Figure 1B:
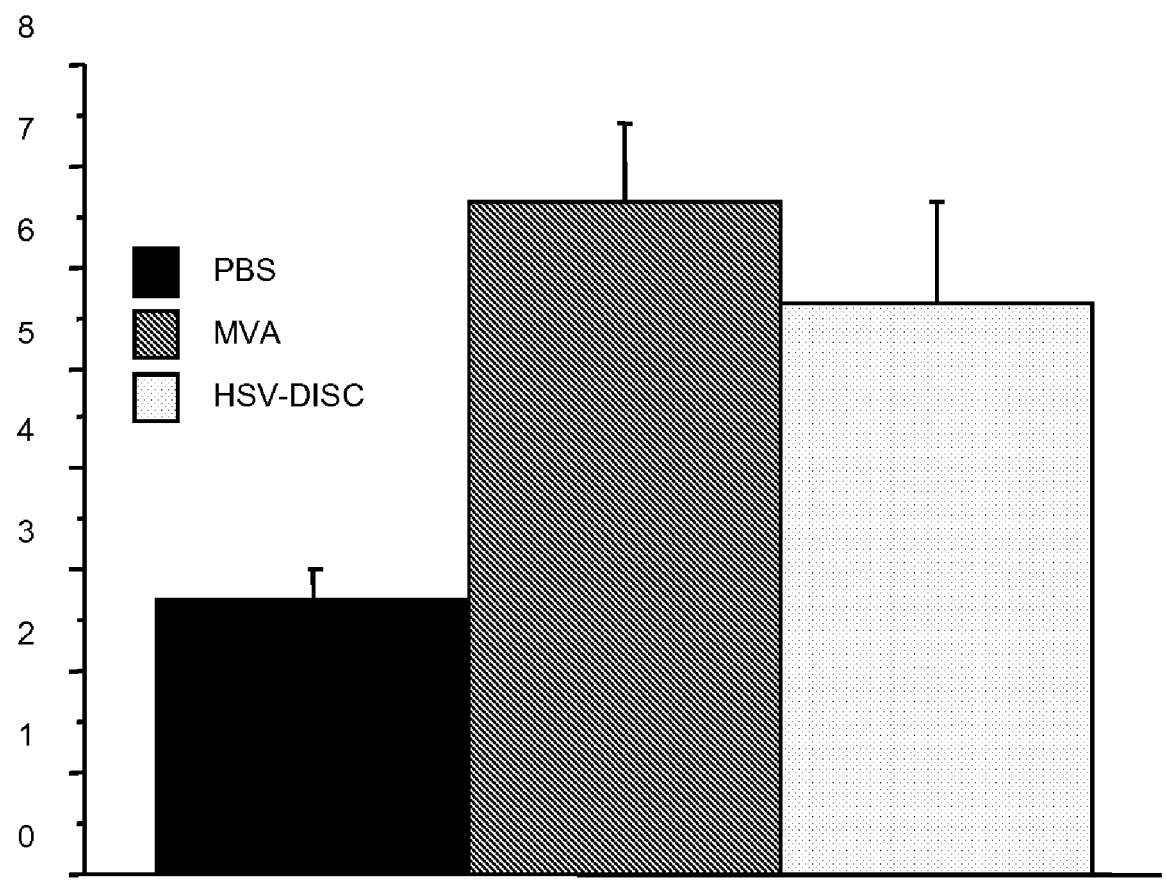

FIG. 1B: The experiment was conducted as indicated for FIG. 1A. However, CD11c cells were determined in spleen by flow cytometry.

Figure 1C:
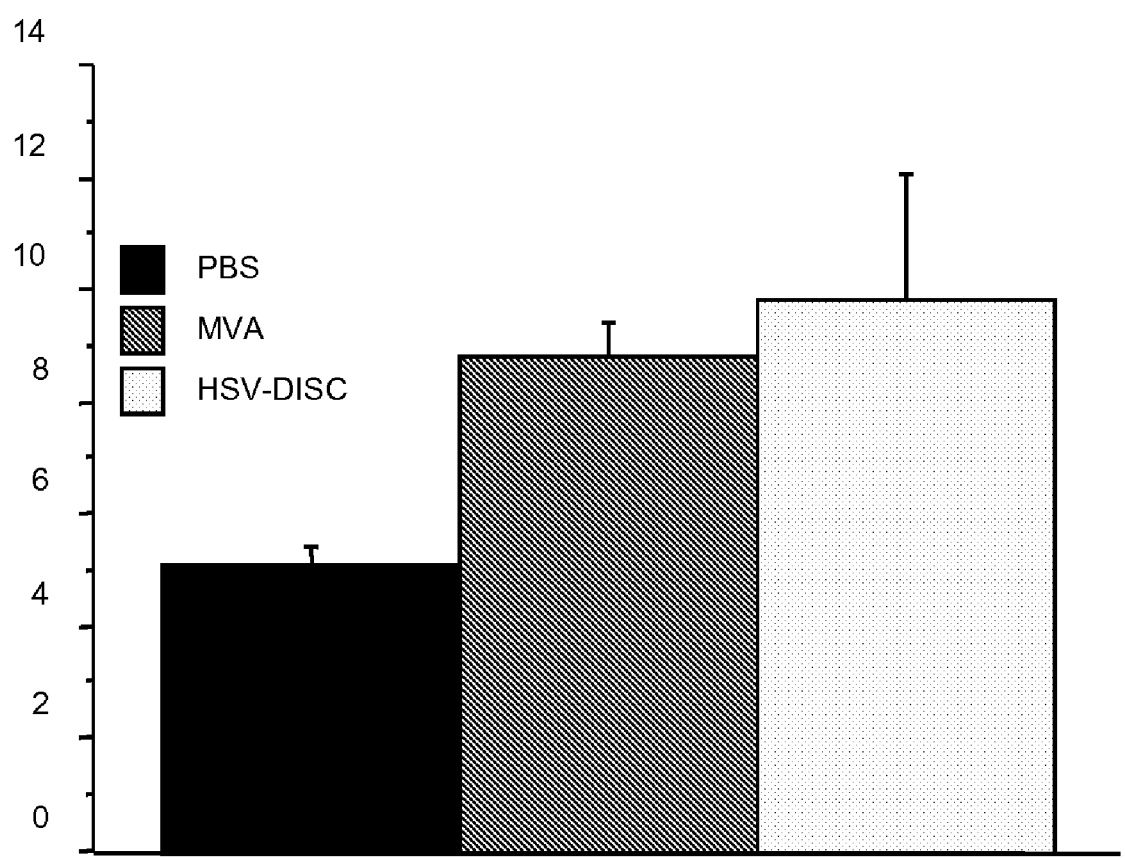

FIG. 1C: The experiment was conducted as indicated for FIG. 1A. However, CD11c cells were determined in peritoneal fluid by flow cytometry.

FIG. 2: Mice were vaccinated with MVA-BN as indicated in the left column. After two weeks, the percentage of $CD11c^+$ single and $CD11c^+/CD8^+$ double positive cells in spleen and in blood were determined by flow cytometry.

Figure 3:
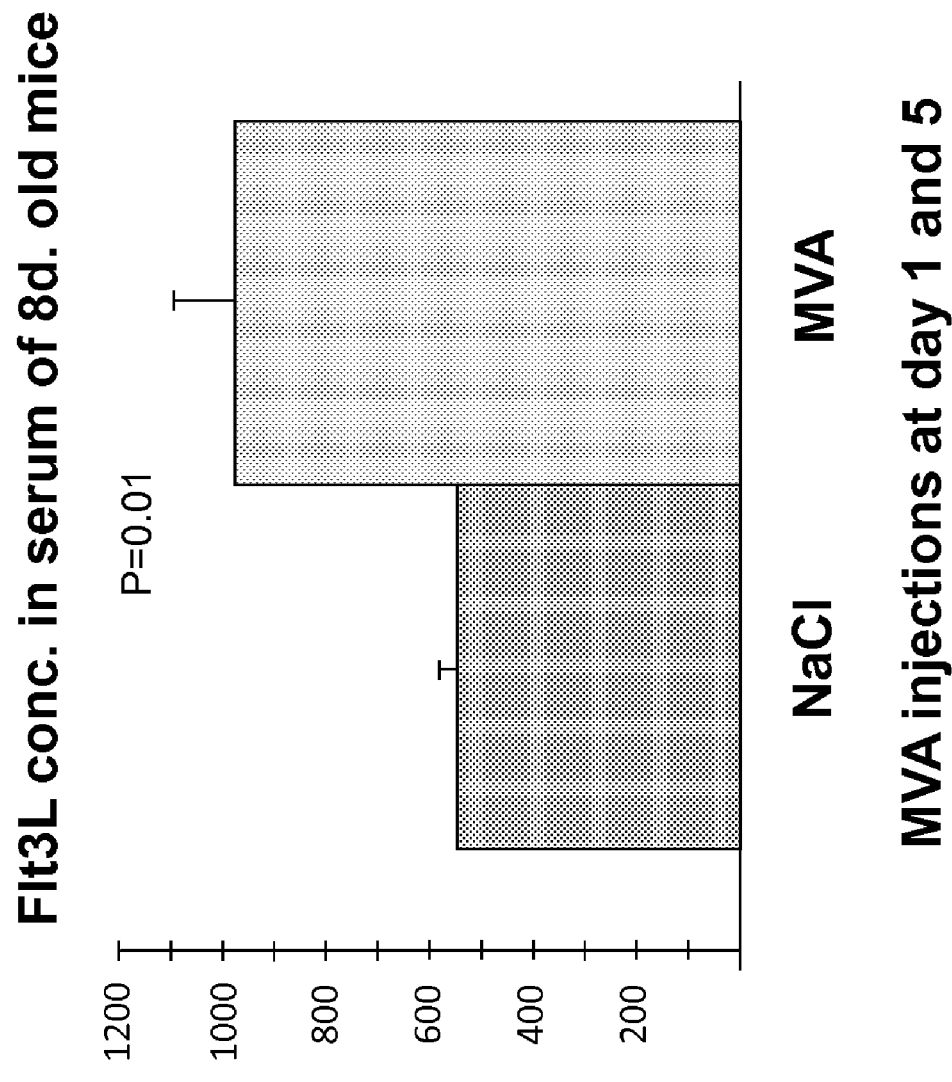

FIG. 3: Newborn mice were injected with MVA or NaCl, as a control, at day one and 5 of age. At day 8, murine Flt3-L was determined in serum of these mice by ELISA and the values are given as pg/ml.

Figure 4:
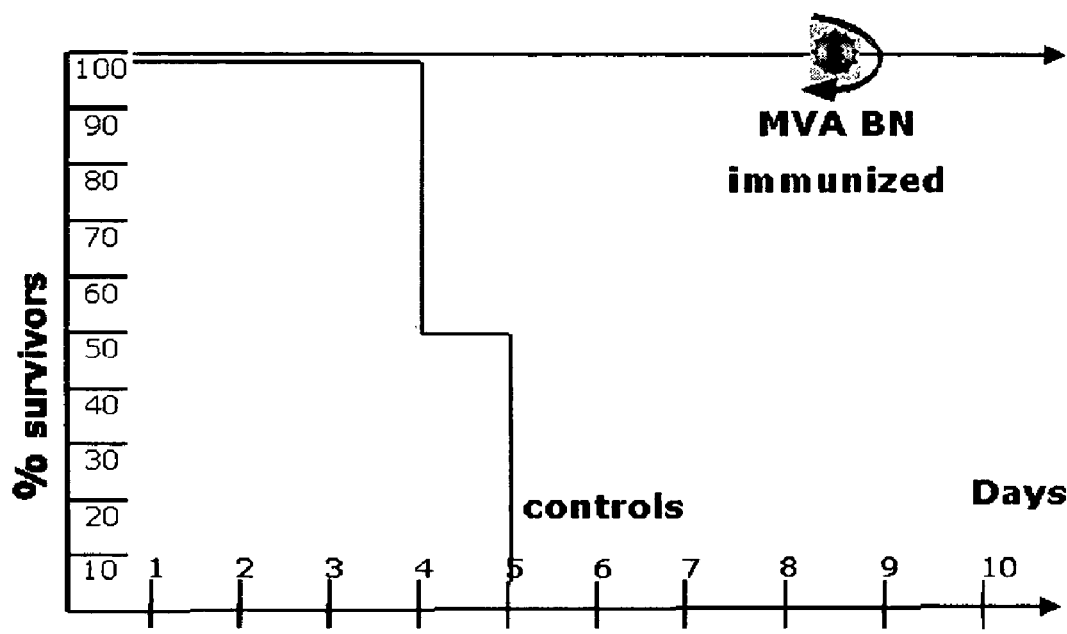

FIG. 4: Newborn mice were injected once within 24-48 h of birth with $10^6$ p.f.u. of MVA or treated with NaCl, as controls. At 7 days of age, all mice were exposed to $100 \times LD_{50}$ of HSV-1 strain F. The number of surviving animals was monitored for 21 days.

FIG. 5: Mice were treated as indicated for FIG. 4. The data represent 9 different challenge experiments with $100 LD_{50}$ of HSV-1. None of the control animals survived the challenge.

Figure 6:
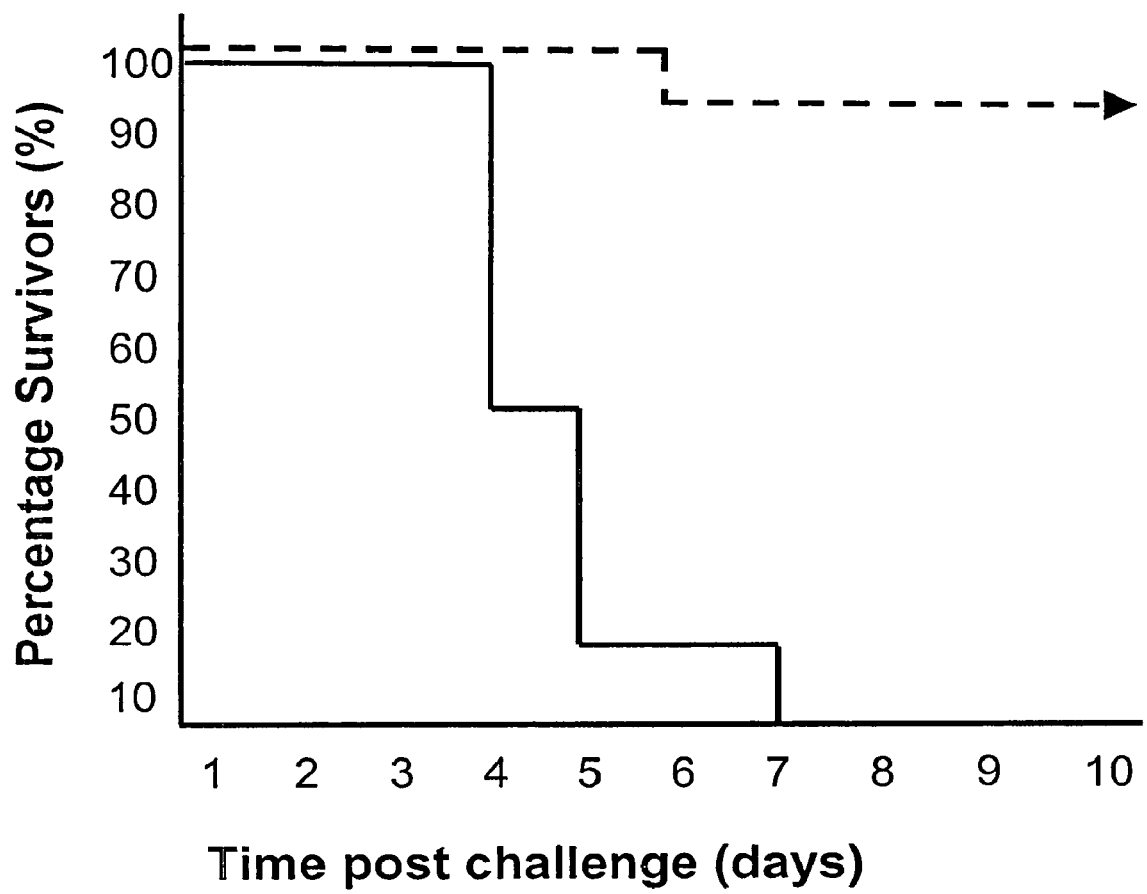

FIG. 6: Survival of adult mice vaccinated on the first day of life with MVA-BN following a lethal vaccinia challenge. Three litters of 6, 1-day-old pups (18 mice) were vaccinated with MVA-BN ($2.5 \times 10^7$ $TCID_{50}$) and at 4 weeks (adult mice) challenged with a lethal dose of vaccinia. MVA-BN vaccination clearly induced a protective immunity in neonatal mice that lasted until adulthood.

EXAMPLES

The present invention will be better understood in connection with the following examples, which are intended as an illustration of and not a limitation upon the scope of the invention.

Example 1

(i) MVA-BN and DISC-HSV Induces DC of the $CD11c^+$ and $CD8^+$ Phenotype in Newborn Animals First set of experiments: Newborn mice are naturally immunodeficient because the IFN system is not mature. Dendritic cells can be induced in vitro, as well as in vivo, by a variety of stimuli. The number and activation state of DC, the best producers of IFN, is evaluated using flow cytometry. In these studies it was determined whether a controlled MVA-BN replication could induce DC, which is evaluated phenotypically. Groups of mice were injected with $10^6$ plaque forming units (p.f.u.) of MVA-BN or saline within 1-2 days after birth, and in some cases 5 days after birth. Blood and spleen cells from individual mice of both groups were analyzed by FACS and the data compared.

Data from 7 to 8 individual mice indicate that treatment with MVA-BN increased $CD11c^+$ cells 2-3 fold, accompanied with increased expression of MHC II and increased presence of T cells of the CD4 or CD8 type. Interestingly, CD19/54, a marker for mature B cells, decreased indicating that these cells either emigrated in organs other than spleen or that precursors of B cells were recruited early to other lineages, notably DC of the plasmacytoid phenotype that carries early B cell markers (B220).

Data from three different experiments indicated reproducibility and significant differences. Experiments with DISC-HSV-1, a different replication controlled viral vaccine, demonstrates the induction of similar amounts of CD11c+ cells after neonatal priming.

The results are summarized in FIG. 1A-C.

To further investigate subpopulations of DC in blood and spleen, and analyze the long-term effect of treatment with MVA-BN, cells in blood and spleen were analyzed at 2 weeks of age. At this time point, treated animals had about twice the number of $CD11c^+$ cells in spleen than the amount observed at one week of age. A single treatment with the virus at birth, resulted in a 3-fold elevated number of these cells in spleen 2 weeks later (FIG. 2). Similar effects were seen in blood, with the exception that the population of CD11c+/CD8a+ were about 4 times higher. A single treatment with MVA-BN at 7 days after birth, leads to an increase of CD11c+/CD8a+, from 13- to 40-fold, with a less dramatic effect on the $CD11c^+$ cells. As expected, two vaccinations, at birth and at day 7, had a significant effect on the population of $CD11c^+$ cells. The various effects are shown in FIG. 2.

In a second set of experiments, one-week-old mice that were vaccinated at birth with $2.5 \times 10^7$ $TCID_{50}$ of MVA-BN showed a different composition of immunologically relevant cell populations in spleen and blood when compared to control mice (Table 1). In blood, there was an increase in the CD8 positive lymphocyte population, as well as an increase in the number of NK cells. The number of CD11c positive cells was about 3 times higher than in controls and the percent of B-cells (B220 and CD19 double positive cells) was significantly decreased. In the spleen, the total number of cells did not differ between immunized animals and controls. In contrast to the blood, the spleen of vaccinated animals had more CD4 positive T lymphocytes than controls and the number of NK cells was not increased. Similar to blood, the relative number of CD8 positive lymphocytes was increased and the number of B-cells decreased. The percentage of CD11c positive cells was about 3 times higher than in controls. A difference in the percentage of dendritic cells was recognized at day 5 following vaccination with MVA-BN, wherein the number of CD11c positive cells in the spleen of 4, untreated controls was 3.6%, compared to 4.8% in the 4, MVA-BN vaccinated mice. The same amount of UV-inactivated MVA-BN did not cause any significant change in the cell populations after vaccination of neonatal mice compared to controls (data not shown). The initial vaccination dose was chosen arbitrarily. After titration of the inoculum, a standard dose of $2.5 \times 10^6$ $TCID_{50}$ was selected for vaccination (10 times less than in the initial experiment). At this dose maximal numbers of DC were induced (Table 2).

significantly higher in MVA-BN treated mice (5.6±0.7%) than in both control groups (untreated 3.0±0.3%, p=0.01; UV-inactivated MVA-BN 3.0±0.2%, p=0.006. Mann-Whitney U-test).

(iii) Neonatal Mice Treated with MVA-BN Have Elevated Levels of Serum Flt3-L

Flt3-L is a hematopoetic factor that leads to increased levels of DC in adult animals. In humans and possibly mice, the richest source of this factor are activated T cells. To determine whether the elevated numbers of DC could be the result of induced Flt3-L, serum of MVA-BN treated mice was compared to mock treated animals for the presence of this factor. Animals treated at day 2 and 5 had twice the levels of Flt3-L in the serum when compared to serum of mock treated animals. Hence, Flt3-L is one of the factors that could be made responsible for elevated numbers of DC (FIG. 3)

The time course of the Flt3-L induction in newborn mice was assessed after administration of MVA-BN. In newborns, MVA-BN vaccination induced an increase in Flt3-L concentration within 24 hours. The induction reached a maximum after 48 hours and was still present at day 7, the time when spleen cells were usually analyzed and resistance against HSV-1 was tested (see below). In the vaccinated mice the Flt3-L concentration in the serum was two-fold increased 24 hours and 48 hours after the vaccination, compared with age matched control animals.

Role of MVA-BN-Induced type I IFN in Resistance Against HSV-1 Challenge.

The ability of MVA-BN to induce IFN type I in newborn mice was evaluated. Elevated levels of serum IFN-alpha was not detected in neonatal or 12-day-old mice 2 days after exposure to MVA-BN. In contrast, cultures of pDC from 1 week old mice infected in vitro with MVA-BN at a multiplicity of infection of 1, secreted ~1000-1500 U of IFN-alpha/$10^5$ cells. In uninfected cultures, no IFN-alpha was detected. Thus, MVA-BN was demonstrated to induce secretion of IFN-alpha in vitro and expansion of DC in vivo.

In an effort to determine whether the IFN type I, which was induced after MVA-BN administration, increased protection, $10^5$ U of rIFN-alpha B/D was injected into naïve mice either once (at birth) or twice (at birth and on the following day) and evaluated for the effect by challenge with HSV-1. Five days after infection, all seven untreated mice were dead. By contrast, six of the seven mice receiving only one treatment, and all seven mice receiving two rIFN treatments, survived for five days. One of the seven mice that received one treatment with IFN, and three of the seven mice that received two

TABLE 1

Changes induced in blood and spleen cells in newborn mice 1 week after immunization with $2.5 \times 10^7$ $TCID_{50}$ MVA-BN

| Parameter % | Blood | | | Spleen | | |
|---|---|---|---|---|---|---|
| | NaCl | MVA-BN | P* | NaCl | MVA-BN | P* |
| Total cells × $10^6$ | | | | 17.9 ± 1.9 | 24.1 ± 2.6 | 0.105 |
| % CD11c | 5.4 ± 1.3 | 18.6 ± 1.5 | 0.001 | 2.8 ± 0.1 | 7.9 ± 0.8 | 0.001 |
| % CD11c/CD8α | 0.5 ± 0.1 | 2.7 ± 0.3 | 0.001 | 1.1 ± 0.1 | 4.6 ± 0.7 | 0.002 |
| % CD4/CD3 | 16.9 ± 1.1 | 16.1 ± 1.5 | 0.999 | 4.8 ± 0.3 | 8.1 ± 1.5 | 0.004 |
| % CD8α/CD3 | 6.0 ± 0.9 | 10.3 ± 0.9 | 0.002 | 4.7 ± 0.3 | 8.4 ± 1.1 | 0.002 |
| % NK1.1/DX5 | 16.4 ± 1.2 | 24.4 ± 3.3 | 0.032 | 2.5 ± 0.3 | 2.4 ± 0.2 | 0.862 |
| % CD19/B220 | 22.3 ± 0.5 | 8.4 ± 0.8 | 0.001 | 16.2 ± 1.3 | 8.6 ± 0.9 | 0.004 |

*Mann-Whitney U-Test

TABLE 2

Induction of CD11c positive cells in the spleen within 7 days after MVA-treatment of 1-day-old wt mice or mice with gene-targeted disruptions.

| Mouse strain | MVA dose ($TCID_{50}$) | controls % CD11c | MVA-BN % CD11c | ratio |
|---|---|---|---|---|
| wt[a] | $2.5 \times 10^7$ | 2.8 | 7.9 | 2.8 |
| wt | $2.5 \times 10^6$ | 2.1 | 11.9 | 5.6 |
| wt | $2.5 \times 10^5$ | 2.5 | 6.6 | 2.6 |
| RAG[b] | $2.5 \times 10^7$ | 4.2 | 5.4 | 1.3 |
| AG129[c] | $2.5 \times 10^3$ | 2.6 | 2.7 | 1.0 |

[a]Wt = either C57BL/6 or 129 Sv/Ev mice.
[b]RAG mice deletion in recombination activating gene (i.e. no functional T and B cells).
[c]AG129 gene targeted disruptions of IFN receptor Type I (IFN-alpha and -beta) and Type II (IFN-gamma)

(ii) MVA-BN Induces Preferentially Plasmacytoid Dendritic Cells (pDC)

According to other authors CD11c positive cells that also expressed CD45RA or CD45R were considered as pDC (Asselin-Paturel, et al. 2001, *Nat Immunol*, 12: 1144). It was, therefore, determined whether MVA-BN induced an increase of pDC. A further experiment was performed in which also CD45RA or CD45R on CD11c positive were analysed. The percentage of CD11c and CD45R double positive cells was treatments with IFN, were still alive at day 21, which means that they survived the challenge.

Example 2

MVA-BN Treated Neonatal Mice Survive a Challenge with 100 to 500 LD$_{50}$ of HSV-1

Groups of mice were treated with the standard dose of MVA-BN one or 2 days after birth and challenged at 7-8 days of age with 100 to 500 LD$_{50}$ of Herpes simplex virus 1 (HSV-1) (FIG. 4). MVA BN treated mice survived the challenge with HSV 1, whereas all the control mice died within 5-6 days after inoculating the challenge virus.

To further support these observations, 9 challenge experiments were performed with 40 MVA BN treated and 45 control mice. More than 80% of the virus treated mice survived the challenge, whereas all the control mice died (FIG. 5).

In a separate set of experiments the mice were treated at birth with MVA-BN (2.5×10$^6$ TCID$_{50}$/mouse). At day 8 a challenge with either 10$^3$ (1 LD$_{50}$) or 10$^5$ (100 LD$_{50}$) PFU of HSV-1 was performed. Following MVA-BN vaccination 65% of the mice survived a viral dose that killed 100% of the control mice (100 LD$_{50}$) and 90% survived a dose that killed 45.5% of the controls (1 LD$_{50}$). In additional experiments a group of 7 mice vaccinated with UV-inactivated MVA-BN were infected with HSV-1. Five of them died within 7 days. The remaining 2 animals ceased to grow and died at day 22 and 29. Therefore, mice treated with MVA-BN reached a state of increased resistance against HSV-1 that was associated with live MVA-BN, but not UV-inactivated MVA-BN.

In control experiments done with mice that do not have functional T-cells it was determined that the protection against HSV-1 after vaccination with MVA-BN was not due to cross-reacting cytotoxic T-lymphocytes induced by MVA-BN.

It was tested whether DC cells were responsible for the protection of mice from HSV-1 after vaccination with MVA-BN. To this end, naïve 8-day-old mice were challenged with 5×10$^4$ PFU HSV-1 4 hr after transfer of cells from MVA-treated mice. In a first experiment splenocytes from 8-day-old mice treated at 1 day of life with MVA-BN were separated in DC rich (low-density) and DC poor (high-density) fractions. Mice receiving 5×10$^6$ cells from the DC rich fraction survived the challenge to 50% whereas all the mice receiving 10 times less DC rich suspension or untreated mice died within 5 days. A second approach was done by transferring positively isolated CD11c positive cells from 8-day-old mice treated at 1 day of life with MVA-BN to naïve age matched mice. A suspension of 2×10$^6$ splenocytes containing more than 80% CD11c positive cells from MVA-BN treated mice protected naïve mice from HSV-1 infection. In contrast, 4 untreated littermates, as well as 8 additional untreated animals, died after the challenge. Furthermore, mice receiving the same amount of spleen cells or mice receiving one spleen equivalent (50×10$^6$ cells) from the negative fraction did not show increased resistance against HSV-1. Thus CD11c positive cells are able to protect mice from HSV-1.

After administration of MVA, short-term protective effects in the range of about 24 hours were described in the prior art (Vilsmeier, B., Berl. Münch. Tierärztl. Wschr. 112 (1999), 329-333). Although the viruses used in said publication are not viruses that are not capable of being replicated to infectious progeny virus in the neonatal or prenatal animal used, it was tested whether the mode of action as disclosed in Vilsmeier is similar to the mode of action described in the present application. More particularly, Vilsmeier discloses that MVA, in particular inactivated MVA, induces a paramunity for about 24 hours. To test whether the paramunity effect counts also for the protective effects as disclosed in the present application mice 24 hours of birth were vaccinated either with MVA-BN or with inactivated MVA-BN. At 7 days of age the mice were challenged with a lethal dose of HSV-1 (10$^5$ PFU HSV-1). Unvaccinated control mice died 6 days after challenge. Also the mice vaccinated with inactivated MVA-BN were not protected against a challenge with HSV-1. The number of DC cells in these mice was not elevated. In contrast, the mice vaccinated with non-inactivated MVA-BN were significantly protected against a challenge with HSV-1. 30 days after the challenge more than 80% of the mice were still alive. Two days after vaccination elevated serum Flt3-L was found in the serum. Elevated numbers of DC were found in the spleen. The enhanced Flt3-L was associated with elevated numbers of DC. This confirms that paramunity effects are not responsible for the observed protection.

(ii) MVA-BN Induces a Specific Immunity in Neonates that Lasts Until Adulthood

One-day-old C57Bl/6 mice (group size of 18) were vaccinated (i.p) with MVA-BN (2.5×10$^7$ TCID$_{50}$). Four weeks after vaccination, when the mice were considered adults there where challenged with a lethal dose (1×10$^4$ TCID$_{50}$) of vaccinia Western Reserve (VV-WR). With the exception of one animal all other MVA-BN vaccinated animals survived. In contrast, all placebo vaccinated animals died within 7 days and demonstrated severe clinical symptoms such as ruffled fur, weight loss and reduced activity. Clearly this is a clear demonstration that MVA-BN vaccination is not only safe in neonatal animals, but is capable of inducing a protective immune response against a lethal vaccinia (related virus to MVA-BN) infection.

Example 3

(i) The Long-Term, But Not Short-Term, Anti Viral Effect of IFNα/β Depends on FL and pDC 3.1 Introduction Treatment of newborn mice with MVA-BN increases resistance against infection with heterologous Herpes simplex virus type 1 (HSV-1) one week after MVA-BN treatment (see above). The protection is associated with increased levels of FL in serum and increased numbers of pDC.

In this example, the role of IFNα and FL (Flt-3L) in the defense against HSV-1 in neonatal mice was investigated. The data show that there is a FL-independent, short-term and a FL-dependent, long-term effect of IFNα. During the long-term effect, IFNα induces FL which is able to increase the number of pDC. Although protection against HSV-1 is not solely dependent on pDC, they play an important role in the defense against HSV-1 in neonatal mice.

3.2 Results 3.2.1 The Short-Term Protection Induced by rIFNα is FL-Independent

As previously shown (Vollstedt, 2003, J. Exp. Med. 197: 575), rIFNα treatment of C57BL/6 mice at day 6 of age, increased resistance against HSV-1 challenge at day 7. The $LD_{50}$ of untreated, neonatal C57BL/6 mice is $10^3$ pfu of HSV-1. This $LD_{50}$ was increased 10-fold to $10^4$ pfu of HSV-1 after rIFNα treatment.

To analyze a possible cooperation between IFNα and FL in the defense against HSV-1, FL-gene deleted (FL-/-) mice were used. It was shown that these animals were very susceptible to HSV-1 infection. As few as 50 pfu of HSV-1 killed 100% of 7-day-old neonates. Treatment with rIFNα at day 6 of age increased resistance, so that 80% of the FL-/- mice survived $5\times10^3$ pfu HSV-1 challenge at day 7, while all untreated FL-/- neonates died. Thus, rIFNα is demonstrated to confer protection during an infection with HSV-1, even in the absence of FL.

3.2.2 The Short-Term Protection Induced by MVA-BN is FL-Independent

As previously shown, MVA-BN, an efficient inducer of IFNα,β (Buttner, 1995, Vet. Immunol. Immunopathol. 46:237; Vilsmeier, 1999, Berl. Munch. Tierarztl. Wochenschr. 112:329; Franchini, 2004, J. Immunol. 172:6304), is able to increase resistance to neonatal infection with HSV-1 in a IFN-dependent manner. MVA also induces FL in vivo in neonatal mice (Franchini, 2004; J. Immunol. 172:6304) Therefore, it was analyzed whether treatment with MVA at day 5 of age also induced protection against HSV-1 in FL-/- neonates. Indeed, in a dose-dependent manner, MVA-BN was able to protect against HSV-1. A dose of $2.5\times10^6$ MVA-BN protected 80% of the neonatal mice, while a dose of $2.5\times10^4$ MVA-BN did not have any protective effect.

Thus, it was concluded that rIFNα or MVA-BN have a short-term, FL-independent effect on the resistance against HSV-1 in neonatal mice.

3.2.3 The Long-Term Protection of rIFNα is FL-Dependent

MVA-BN treatment within 24 hours of birth was demonstrated to protect against infection with HSV-1 at day 7, when the IFNα,β system was intact, and was demonstrated to elevate FL concentration in serum and DC numbers in spleen in neonatal mice (Franchini, 2004, J. Immunol. 172:6304). Since induction of IFNα occurred very early and viral challenge was one week later, MVA-BN induced long-term protection against viral infections was considered dependent on MVA-induced IFNα and FL. To evaluate the relative contribution of IFN and FL to this long-term effect, treatment with rIFNα or MVA-BN at birth was evaluated for protection against an HSV-1 infection one week post-treatment in FL-/- mice.

C57BL/6 mice were treated with rIFNα at day 0/1 and challenged with HSV-1 at day 7. rIFNα treated mice showed an increased resistance with an $LD_{50}$ of $10^5$ pfu of HSV-1. To determine the dependence on FL, FL-/- neonates were treated with rIFNα at day 0/1 and then infected with $5\times10^3$ pfu HSV-1 at day 7. rIFNα treatment did not show any effect and all treated mice died within the same time interval as untreated controls. MVA-BN treatment of FL-/- mice within 24 hours of birth also did not show any protective effect with any dose used.

Thus, it was determined that rIFNα has a long-term, FL-dependent effect on the resistance against HSV-1 in neonatal mice.

MVA-BN not only induces IFNα, but a plethora of other cytokines, such as IL-2, IL-6, IL-12 and TNF (Buttner, 1995, Vilsmeier, 1999, see above). The production of these cytokines in the absence of FL was not demonstrated to confer any protection against HSV-1.

3.2.4 The Absence of FL Does Not Impair IFNα,β Production In Vitro

The high susceptibility of FL-/- neonates to HSV-1 could have been caused by a FL-dependent inability for IFNα,β production. The capacity of spleen cells from 7-day-old mice to produce IFNα,β in vitro was investigated. After overnight cultivation with HSV-1, at an MOI of 10, spleen cells of FL-/- neonates produced 220 U/ml IFNβ, which was more than cells from C57BL/6 neonates. Production of IFNα by spleen cells of FL-/- neonates was 30 U/ml, while IFNα was not detected in supernatants of stimulated cells from C57BL/6 neonates.

3.2.5 The Absence of FL Leads to Decreased Numbers of DC

To define which cell populations were responsible for the high susceptibility of FL-/- neonates, an extensive phenotyping of spleen cell populations of FL-/- neonates at day 7 was performed. DC's were highly reduced in cell number and had a rather immature appearance with low expression of CD11c and MHCII. No difference in NK and B cell numbers was detected. Treatment with human (hu) or murine (mu) FL reconstituted DC to similar numbers as seen in C57BL/6 mice and increased the relative number of NK cells.

To confirm these data, immunohistology of spleen and liver from 7-day-old FL-/- and C57BL/6 neonates was performed. Numbers of CD11c-positive cells were reduced in spleen and liver of FL-/- neonates when compared to C57BU neonates.

Next, it was determined whether treatment with human and murine FL also reconstituted resistance in FL-/- neonates to C57BL/6 levels. After treatment with huFL for a week FL-/- neonates had an increased $LD_{50}$ of $10^4$ pfu of HSV-1, while treatment with muFL resulted in an $LD_{50}$ of $10^3$ pfu of HSV-1, which equals the resistance of C57BL/6 neonatal mice.

Thus, the cells from FL-dependent progenitors, such as DC, appear to play an important role in the defense against HSV-1 in neonatal mice.

3.2.6 rIFNα Treatment of Wild Type Neonates Increases the Number of pDC rIFNα treatment increases the number and promotes the maturation of DC. C57BL/6 and FL-/- mice were treated with rIFNα and the relative and absolute cell numbers of DC subpopulations in the spleen were investigated.

Flow cytometry analysis revealed that rIFNα treatment of C57BL/6 neonates at day 0/1 increased the number of pDC at 7 days of age. The proportion of pDC to cDC was 0.3:1 in untreated animals, while rIFNα treatment at this time point changed this proportion to 1.2:1. In absolute cell numbers, pDC numbers increased 2-fold and cDC numbers decreased 2-fold in the spleen of day 0/1 treated neonates. Treatment with rIFNα at day 6 changed the proportion of pDC to cDC to 1:1. Expression of CD8α, CD4 and MHC class II was unchanged after any rIFNα treatment.

Thus, it may be concluded that rIFNα treatment leads to an increase of pDC numbers, which is FL-dependent.

3.2.7 rIFNα Induces Increased FL Production

Since treatment with rIFNα increased the numbers of pDC in C57BL/6 neonates with an intact FL system, it was determined whether IFNα itself could induce FL production in these mice. Untreated 1 to 4-day-old mice had moderate levels of FL in the blood serum (450 pg/ml). rIFNα treatment at day 1 resulted in an increase in these levels. As early as 6 hours after treatment, the serum levels were 600 pg/ml, which increased to 1000 pg/ml after 12 hours and peaked at 1400 pg/ml at 24 hours. The FL serum levels started to decrease at 48 hrs to 1300 pg/ml and were close to control levels after 96 hours (700 pg).

Thus, rIFNα is able to induce a higher production of FL in the blood serum of neonatal C57BL/6 mice.

3.2.8 Induction of pDC by FL is IFNα,β-Independent

Since rIFNα was demonstrated to increase the number of pDC, the IFNα,β-dependent development of pDC was investigated. This effect was evaluated in IFNα,β receptor gene-deleted (A129) neonatal mice. By flow cytometry, it was demonstrated that these mice had numbers of splenic pDC similar to C57BL/6 neonates. Treatment with human or murine FL increased the number of pDC, as well as the number of cDC similar to that in C57BL/6 neonates (Vollstedt, 2003, see above).

Thus, although rIFNα induces increased numbers of pDC, the development of pDC can be augmented by exogenous FL treatment in A129 mice.

3.2.9 pDC Play an Important Role in the Defense Against HSV-1 in Neonates

IFNα and pDC have been demonstrated/observed to play an important role in the defense against HSV-1 in neonatal mice. To test the effect of pDC directly, pDC from FL-treated adult mice were transferred into 6-day-old FL−/− mice and infected with HSV-1 at day 7. Control mice usually died around day 5 and 6. Transfer of 5 million pDC into 6-day-old mice increased the rate of survival so that 4 out of 10 mice survived infection after 3 weeks. When 5 million cDC were transferred, the onset of death was later, within a time frame of 8 to 10 days, and only 1 out of 10 mice survived the infection after 3 weeks. Consequently, it may be concluded that pDC are effective for the protection against lethal infection with HSV-1.

The present invention is not to be limited in scope by the specific embodiments described herein. Indeed, various modifications of the invention in addition to those described herein will become apparent to those skilled in the art from the foregoing description.

All patents, applications, publications, test methods, literature, and other materials cited herein are hereby incorporated by reference.

The invention claimed is:

1. A method for increasing the number of dendritic cells (DCs) in a human or mouse neonate comprising administering to the neonate an MVA virus characterized by being capable of reproductive replication in vitro in chicken embryo fibroblasts and by being non-replicative in vitro in the human keratinocyte cell line HaCaT and the human cervix adenocarcinoma cell line HeLa, wherein the administration of the MVA virus increases the number of dendritic cells in the animal.

2. The method of claim 1, wherein the neonate is a mouse.

3. The method of claim 1, wherein the neonate is a human.

4. The method of claim 1, wherein the DCs are CD11c+.

5. The method of claim 1, wherein the DCs are CD45R+.

6. The method of claim 1, wherein the DCs are CD45R+ and CD11c+.

7. The method of claim 1, wherein the DCs are plasmocytoid dendritic cells (pDCs).

8. The method of claim 3, wherein the human neonate is less than 2 months old.

9. The method of claim 3, wherein the human neonate is less than 6 weeks old.

10. The method of claim 2, wherein the MVA is MVA-BN as deposited at the ECACC under deposit number V00083008.

11. The method of claim 3, wherein the MVA is MVA-BN as deposited at the ECACC under deposit number V00083008.

12. The method of claim 2, wherein the MVA comprises at least one heterologous nucleic acid sequence.

13. The method of claim 12, wherein the heterologous nucleic acid sequence encodes a foreign antigen.

14. The method of claim 12, wherein the heterologous nucleic acid sequence encodes a tumor antigen.

15. The method of claim 3, wherein the MVA comprises at least one heterologous nucleic acid sequence.

16. The method of claim 15, wherein the heterologous nucleic acid sequence encodes a foreign antigen.

17. The method of claim 15, wherein the heterologous nucleic acid sequence encodes a tumor antigen.

18. The method of claim 2, wherein the MVA is administered in a first inoculation ("priming inoculation") and a second inoculation ("boosting inoculation").

19. The method of claim 3, wherein the MVA is administered in a first inoculation ("priming inoculation") and a second inoculation ("boosting inoculation").

20. The method of claim 11, wherein the MVA is administered in a first inoculation ("priming inoculation") and a second inoculation ("boosting inoculation").

* * * * *